US008808722B2

(12) United States Patent
Scholz et al.

(10) Patent No.: US 8,808,722 B2
(45) Date of Patent: Aug. 19, 2014

(54) STABLE ANTISEPTIC COMPOSITIONS AND METHODS

(75) Inventors: Matthew T. Scholz, Woodbury, MN (US); Kevin D. Landgrebe, Woodbury, MN (US); Katie F. Wlaschin, St Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/807,035

(22) PCT Filed: Jun. 29, 2010

(86) PCT No.: PCT/US2010/040483
§ 371 (c)(1),
(2), (4) Date: Jan. 10, 2013

(87) PCT Pub. No.: WO2012/002943
PCT Pub. Date: Jan. 5, 2012

(65) Prior Publication Data
US 2013/0108576 A1      May 2, 2013

(51) Int. Cl.
*A61F 13/00*          (2006.01)
(52) U.S. Cl.
USPC ........................................... 424/422; 424/434
(58) Field of Classification Search
None
See application file for complete search history.

(56) References Cited

U.S. PATENT DOCUMENTS

| 4,206,204 | A | 6/1980 | Langford |
| 4,207,310 | A | 6/1980 | Langford |
| 4,271,149 | A | 6/1981 | Winicov |
| 4,597,975 | A | 7/1986 | Woodward |
| 4,867,897 | A | 9/1989 | Kolstad |
| 4,904,480 | A | 2/1990 | Khan |
| 4,954,351 | A | 9/1990 | Sackler |
| 4,996,048 | A | 2/1991 | Bhahwat |
| 5,665,776 | A | 9/1997 | Yu |
| 5,908,619 | A | 6/1999 | Scholz |
| 5,951,993 | A | 9/1999 | Scholz |
| 6,436,445 | B1 | 8/2002 | Hei |
| 6,582,711 | B1 | 6/2003 | Asmus |
| 6,838,078 | B2 | 1/2005 | Wang |
| 7,147,873 | B2 * | 12/2006 | Scholz et al. ................ 424/672 |
| 2003/0194447 | A1 * | 10/2003 | Scholz et al. ................ 424/672 |
| 2005/0089539 | A1 | 4/2005 | Scholz |
| 2006/0051384 | A1 | 3/2006 | Scholz |
| 2006/0051385 | A1 | 3/2006 | Scholz |
| 2006/0052452 | A1 | 3/2006 | Scholz |
| 2006/0177511 | A1 | 8/2006 | Scholz |
| 2009/0068288 | A1 * | 3/2009 | Kruger ......................... 424/670 |
| 2009/0169647 | A1 | 7/2009 | Scholz |

FOREIGN PATENT DOCUMENTS

| WO | WO 89/00006 | 1/1989 |
| WO | WO 2006/099359 | 9/2006 |

OTHER PUBLICATIONS

Novel Gelling Agents Based on Polymer/Surfactant Systems, E.D. Goodard et. al., J. Soc. Cosmet. Chem., 42, 19-34 (Jan./Feb. 1991).
Search report from applicant case No. 66703WO003 Application # PCT/US10/40483 filed Jun. 29, 2010.

* cited by examiner

*Primary Examiner* — Susan Tran

(57) ABSTRACT

Provided are methods of improving the stability of antiseptic compositions that include elemental iodine and certain hydroxycarboxylic acids, as well as stable, ready to use antiseptic compositions suitable for use in the nose and anterior nares.

18 Claims, 1 Drawing Sheet

STABLE ANTISEPTIC COMPOSITIONS AND METHODS

CROSS REFERENCE TO RELATED APPLICATIONS

This application is the National Stage filing under 35 U.S.C. 371 of International Application No. PCT/US2010/040483, filed Jun. 29, 2010.

BACKGROUND

It is a standard practice in the industrialized world to disinfect the skin prior to any invasive procedure such as surgery, catheterization, or needle puncture to reduce the risk of infection. Decontamination of the oral cavity and nasal cavity also has been suggested to reduce the incidence of infection in cardiac surgery and/or to reduce spread of Methicillin Resistant *Staphylococcus aureus* (MRSA) in healthcare facilities. These products are often referred to as skin preps, nasal preps, oral preps, or simply "preps". Recently there has been a number of papers published showing that patients who carry *Staphylococcus aureus* (SA) in their nose at the time of surgery are at much greater risk of acquiring a surgical site infection. It is particularly advantageous to customers to have a single product that can be used on both intact skin and mucosal tissue (e.g., vaginal, oral, nasal, and ocular tissue). Other sensitive tissues that antimicrobial products have been used on include acute and chronic wounds as well as burns.

Elemental (molecular) iodine ($I_2$) has proven to be an outstanding antimicrobial agent for such antiseptic compositions. In many antiseptic compositions, iodine as antimicrobial agent is provided in solution in the form of an "iodophor" which is a complex of elemental iodine or triiodide with certain carriers. These iodophors function to not only increase the iodine solubility but to reduce the level of free molecular iodine in solution and to provide a type of sustained release reservoir of elemental iodine. Of available iodophors, povidone iodine is particularly useful.

Still other components have been shown to further boost the antimicrobial efficacy of elemental iodine. The addition of hydroxycarboxylic acids, for example, to antiseptic compositions as a buffer advantageously results in increased levels of bacterial "kill". U.S. Pat. No. 7,147,873 (Scholz et al.) reports that elevated levels of hydroxycarboxylic acids (above 5% wt/wt) result in significantly improved antimicrobial efficacy. The use of hydroxycarboxylic acids in elevated levels in combination with iodophors like povidone iodine would thus seem rather desirable for most antiseptic compositions.

SUMMARY

While desirable for higher microbial kill, elevated levels of certain hydoxycarboxylic acids shorten the effective life of the antimicrobial composition. The hydroxycarboxylic acid in certain cases tends to ultimately decrease the available free iodine and reduce the stability of the composition. Thus, what is needed is a presurgical prep including elemental iodine and a high level of hydroxycarboxylic acid that is iodine stable and can be used in the nose and particularly in the anterior nares.

The present invention relates to compositions that contain at least one antimicrobial agent intended primarily for tissue antisepsis. Such compositions are particularly useful in prepping the skin and mucosal tissue (including oral tissue, nasal passages including the anterior nares, esophagus, and vagina) prior to an invasive procedure being performed on the subject.

The iodine stable compositions of the present invention include an antimicrobial agent selected from the group consisting of iodine ($I_2$), an iodophor, and a combination thereof, wherein the antimicrobial agent is present in a sufficient concentration to provide an available iodine concentration of 0.1 wt-% to 2 wt-%; a hydroxycarboxylic acid, an iodide salt, and an amine oxide.

Optional components useful in the antiseptic compositions of the present invention may include surfactants, monosaccarides and/or sugar alcohol, polymeric film formers, dyes or pigments, emollients, thickeners, and emulsifiers.

In one aspect, the present invention provides ready to use tissue antiseptic compositions that include an antimicrobial agent selected from the group consisting of iodine ($I_2$), an iodophor, and a combination thereof, with antimicrobial agent present in a sufficient concentration to provide an available iodine concentration of 0.1 wt-% to 2 wt-%. The compositions further include a hydroxycarboxylic acid present at a concentration of at least 2.5 wt-%; an amine oxide; and an iodide salt present in at least a concentration of 2.0 wt-%.

In certain embodiments, the ready to use compositions are iodine stable. In other embodiments, the compositions are also physically stable.

In another aspect, the present invention provides iodine stable, ready to use tissue antiseptic compositions including an antimicrobial agent selected from the group consisting of iodine ($I_2$), an iodophor, and a combination thereof. The antimicrobial agent is present in such compositions at a sufficient concentration to provide an available iodine concentration of 0.1 wt-% to 2 wt-%. These compositions also include a monosaccharide, a sugar alcohol, or a combination thereof; a surfactant; water; a thickener; a hydroxycarboxylic acid present at a concentration of greater than 1.0 wt-%; an amine oxide; and an iodide salt present at a concentration of greater than 2.0 wt-%.

In another aspect, the present invention provides iodine stable tissue antiseptic compositions that include an antimicrobial agent selected from the group consisting of iodine ($I_2$), an iodophor, and a combination thereof, with the antimicrobial agent present in a sufficient concentration to provide an available iodine concentration of 0.1 wt-% to 2 wt-%. Such compositions further include a hydroxycarboxylic acid that is not a hydroxyacetic acid or a citric acid; an amine oxide; and an iodide salt present in at least a concentration of 2.0 wt-%.

The present invention also provides methods of stabilizing tissue antiseptic compositions including an iodophor and a hydroxycarboxylic acid. In one aspect, the method includes providing a tissue antiseptic composition comprising: an antimicrobial agent selected from the group consisting of iodine ($I_2$), an iodophor, and a combination thereof, with the antimicrobial agent present in a sufficient concentration to provide an available iodine concentration of 0.1 wt-% to 2 wt-%; and a hydroxycarboxylic acid. The methods further include providing an amine oxide and an iodide salt; and mixing the amine oxide and the iodide salt with the tissue antiseptic composition to form a stabilized composition. In the stabilized composition of these methods, the amine oxide is present at a total concentration of 0.25 wt-% to 1.5 wt-% and the iodide salt is present at a total concentration of about 1.5 wt-% to 10 wt-%.

In another aspect, the prevent invention provides methods of disinfecting the nasal passages of a patient that includes applying the tissue antiseptic compositions of the present invention to the nasal passages of the subject.

In another aspect, the prevent invention provides methods of disinfecting the tissue of a patient that includes applying the tissue antiseptic compositions of the present invention to the tissue of the subject.

The term "iodine stable" refers to a composition that does not suffer a loss of greater than about 25% wt/wt in the available iodine from the original value (i.e., concentration) when aged in a closed (i.e., sealed and does not allow evaporation of any of the components) and unreactive container at 40° C. for about 6 months.

The terms "tissue antiseptic composition," "antiseptic composition," "composition," "skin prep," and "prep" herein refer to a composition that is active against (i.e., effective at killing and/or deactivating) at least one species of bacteria on skin and/or mucosal tissue.

The term "amine oxide" includes compounds, oligomers, and polymers comprising one or more amine oxide groups and compounds comprising a single amine oxide group.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an antimicrobial composition that comprises "a" surfactant can be interpreted to mean that the antimicrobial composition includes "one or more" surfactants.

As used herein, the term "or" is generally employed in its sense including "and/or" unless the content clearly dictates otherwise.

The term "and/or" means one or all of the listed elements or a combination of any two or more of the listed elements (e.g., killing and/or inactivating a bacterium means inactivating, killing, or both inactivating and killing the bacterium).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further described with reference to the drawings, wherein corresponding reference characters indicate corresponding parts throughout the several views, and wherein.

DETAILED DESCRIPTION OF ILLUSTRATIVE EMBODIMENTS

Figure 1:
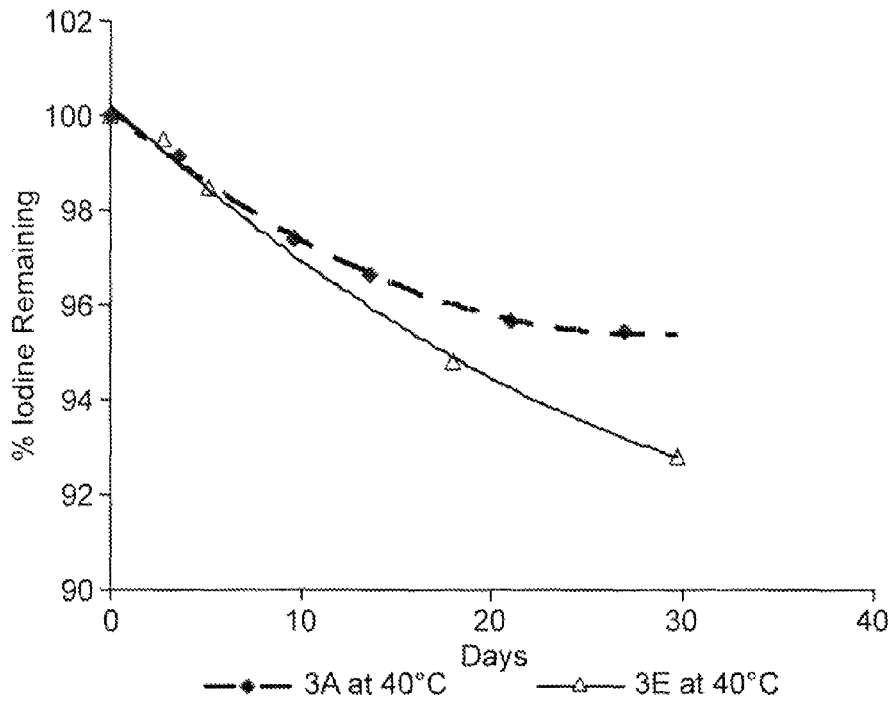
FIG. 1 is a graphical representation of the loss of available iodine over time according to Examples 3A and 3E.

The present invention provides iodine stable tissue antiseptic compositions that include iodine (preferably provided in the form of an iodophor), a hydroxycarboxylic acid, an iodide salt, and an amine oxide.

Antiseptic compositions of the present invention have one or more of the following properties: relatively high levels of bacterial kill; relatively rapid speed and/or length of bactericidal activity; not likely to generate bacterial resistance; capable of delivering iodine over a period of time; suitable for use on sensitive tissues such as mucosal tissue including vaginal, oral, esophageal and nasal tissue; relatively nonirritating to a majority of patients; acceptable odor; acceptable taste in the event some of the composition is deliberately used in the oral or esophageal cavity or if the composition is placed in the nose and migrates up the nasal passages and down the throat; good adhesion to the skin and/or mucosal tissue when both wet and dry; sufficiently high viscosity to provide substantivity to mucosal tissue such that the residence time in the nose or other mucosal tissue (e.g., oral, vaginal, or esophageal) is increased over a non-thickened formulation; preferably good adhesion of pressure sensitive adhesive (PSA) coated products such as incise drapes, tapes, wound dressings, and the like, over the dried prep on skin (preferably, for long periods of time, e.g., hours to days); resist lift off of PSA-coated products over the dried prep on skin while under stress as typically occurs during retraction in surgery; can be removed relatively easily, preferably without the need for organic solvent-based removers and does not loose more than 20% wt/wt iodine (and preferably not more than 10% wt/wt iodine) over the shelf life of the product.

Preferred antiseptic compositions of the present invention possess many or all of the above-mentioned characteristics. Significantly, they provide rapid broad spectrum microbial kill, with very little or no chance of bacterial resistance, are well tolerated on mucosal tissue, and have an acceptable odor and taste. Furthermore, they are gentle to tissue and can be removed with a water-soaked or soap and water soaked fabric, such as a towel or simple gauze.

The compositions are iodine stable at relatively high iodine concentrations used in the "ready to use" composition, in that they feature more available iodine (and thus more antimicrobial efficacy) after significant periods of storage than certain other iodophor containing antimicrobial compositions that include elevated levels of hydroxycarboxylic acids. Certain embodiments do not suffer a loss of greater than about 15% wt/wt in the available iodine from the original value, and more preferably 10% wt/wt, and even more preferably 5% wt/wt when aged in a closed and unreactive container at 40° C. for about 6 months. As used herein "ready to use" refers to the composition intended to be applied (e.g. to skin or mucosal tissue) without dilution.

Preferred compositions of the present disclosure are also physically stable, in that they show no indicia of visible gross phase separation (e.g., precipitation, phase split, settling) after storage at about 50° C. for 15 days. While certain embodied compositions may become slightly cloudy during the 15 day storage period, the absence of gross precipitation and/or settling means these samples may be considered physically stable. Other compositions of the present invention show no visible changes, i.e., no changes in color or clarity. Also certain compositions of this invention may be thickened with emulsifier systems that form emulsions and dispersions. These systems are considered physically stable if there is no syneresis and if the viscosity does not drop to less than half the initial viscosity when aged for 30 days at 40° C. and allowed to equilibrate at 23° C. for 24 hours.

Preferred compositions of the present invention are also generally substantive. More preferred compositions of the present invention are substantive while in moist environments, such as the nose, anterior nares, and vaginal vault and remain on any of these tissues for longer periods of time than typical antiseptics such as BETADINE 10% povidone-iodine solution (Purdue Frederick, Norwalk, Conn.).

A "substantive" composition is one that when placed in the anterior nares has visible iodine still present 30 minutes (min) in a majority of subjects after instillation of 0.25 milliliter (mL) with a cotton bud and gently massaging the nostrils for 30 seconds to ensure an even distribution (as long as the patient does not discharge or deliberately or inadvertently wipe the product away). Preferred substantive compositions remain present in the anterior nares for 45 min, and more preferably for 60 min, post instillation. This is conveniently determined by dabbing the inside of the anterior nares with a white tissue such as a KLEENEX tissue or by imparting color to the composition (e.g., inclusion of a small amount of a dye or a colored active such as povidone-iodine in sufficient concentration that a relatively dark color results on the skin that can be easily seen as present or not).

Many of the compositions of this invention are also "skin substantive" and thus a composition applied and allowed to dry resists removal from skin for at least 15 seconds when tested as described in the "Substantivity Test" described in U.S. Pat. No. 7,147,873 (Scholz et al). For use on skin, the compositions may be even more substantive and resist being removed under the same conditions for at least 30 seconds, more preferably at least 45 seconds, and most preferably at least 60 seconds. This is conveniently determined by imparting color to the composition (e.g., inclusion of a small amount of a dye or a colored active such as povidone-iodine in sufficient concentration that a relatively dark color results on the skin that can be easily seen as present or not).

The dried films of preferred antiseptic compositions of the present invention that include a film-forming polymer are generally flexible and durable. That is, they do not crack or flake off as brittle films might do. Significantly, film-forming polymers contribute to achieving a delicate balance between low tack and flexibility.

Although antiseptic compositions of the present invention can be of a wide variety of viscosities, preferred compositions possess viscosities that ensure the formulations go on easily and form a substantive film, particularly on wet tissue (such as mucosal tissue). Preferably, the Brookfield viscosity of a composition is greater than 100 Centipoise (cps), more preferably greater than 500 cps, even more preferably greater than 1000 cps, even more preferably greater than 2000 cps, and most preferably greater than 5000 cps. Certain skin antiseptic compositions of the present invention resist removal particularly well after they are dry. These compositions generally have lower viscosity (e.g., less than 1000 cps), and preferably greater than 10 cps. Viscosities herein are measured at 23° C. using a Brookfield LVT viscometer and the procedure described in the Examples Section.

A relatively low viscosity ensures that the composition can be painted on the skin or mucosal tissue with little effort in a uniform thin film that may dry rapidly. Thus, the viscosities of preferred compositions for use on intact skin of this invention are no greater than 500,000 cps, preferably no greater than 200,000 cps, more preferably no greater than 50,000 cps, still more preferably no greater than 10,000 cps, and most preferably no greater than 5,000 cps. For use on skin the composition may have a viscosity of less than 100 cps. For use on wound or musocal tissue, such as in the nasal cavity or vagina, the viscosity is preferably relatively high to minimize drainage and mess, preferably no greater than 20,000 cps. On wound and mucosal tissue the composition may not dry in use. Thus, the high viscosity helps to maintain the composition at the application site for extended periods of time to improve microbial kill.

A particularly important property of antiseptic compositions of the present invention for use on skin, wound, or mucosal tissue is the ability to reduce the bacterial load on tissue, particularly skin (e.g., to kill the natural skin flora), rapidly. Preferably, compositions of the present invention are capable of reducing normal skin flora by at least 1 log (10-fold), more preferably by at least 1.5 log, and most preferably by at least 2 logs (100-fold), in 2 minutes on a dry human skin site (typically, skin on an abdomen or back) using ASTM testing method E1 173-93 and a 30-second scrub with gauze soaked in the composition using moderate pressure.

This rapid and high antimicrobial activity is provided through the use of iodine, preferably delivered as an iodophor to reduce irritation potential, as the active antimicrobial agent. The compositions of the present invention further comprise one or more hydroxycarboxylic acid buffers in particularly high use concentrations. The elevated concentrations of hydroxycarboxylic acids in the compositions contribute significantly to an increase in bacterial kill. By comparison, a composition of the present invention reduces normal skin flora by at least 0.5 log more than the same composition without the hydroxycarboxylic acid buffer present. This "same" composition includes additional water instead of the hydroxycarboxylic acid buffer and would be adjusted to the same pH as the composition with these components using a mineral acid or base, such as hydrochloric acid or sodium hydroxide that does not compromise the stability of the composition. The placebo compositions (i.e., compositions without an antimicrobial agent but still including the hydroxycarboxylic acid buffer) are relatively inactive. By comparison, a composition of the present invention reduces normal skin flora by at least 0.5 log more than the same composition without the iodine or iodophor present when tested on a dry human skin site (e.g., back or abdomen) according to ASTM testing method E1173-93 measured 2 minutes after completion of a 30-second scrub with gauze soaked in the composition using moderate pressure.

Generally, antiseptic compositions are applied to the tissue, typically skin, and allowed to dry and remain in place for at least 2 minutes, and often for several hours to days. Significantly, many of the compositions of the present invention maintain very low bacterial counts on the tissue, typically skin, for long periods of time, e.g., often up to 6 hours, and even up to 24 hours.

Antimicrobial Agents

A preferred active antimicrobial agent is elemental iodine ($I_2$), which can be provided in the form of an iodophor. As in most iodine-containing patient preps, other iodine-containing species may be present in addition to iodine. Such species include, for example, hypoiodous acid (HOI), iodide ($I^-$), triiodide ($I_3^-$), iodate ($IO_3^-$), and the like. It is widely recognized that elemental iodine is the most active antimicrobial species. See, for example, Disinfection, Sterilization, and Preservation by Seymour S. Block, $4^{th}$ edition, Chapter 8 "Iodine and Iodine Compounds," Lea & Febiger, Philadelphia, Pa., 1991. Minor amounts of $Br^-$ and or $Cl^-$ also may be present.

In most commercially available iodine disinfectants, in order to prevent rapid reduction of iodine to iodide the solutions are typically buffered to be slightly acidic (e.g., 6 or less, and often 2 to 6). Compositions that are too acidic can be irritating. The acidity is typically desired to maintain stability in the iodine solutions and to suppress conversion to other iodine species that are less germicidal. For example, commercial skin preps containing iodine generally have pH values in the range of 3 to 6, which favors stability of the molecular iodine species. HOI normally exists in very low levels relative to $I_2$ but has been reported as an effective antimicrobial and may contribute to kill in some compositions. $IO_3^-$ is an effective oxidant only at pH values less than 4, where significant amounts of $HIO_3$ can exist.

As further background for understanding and practicing the present invention, elemental iodine is only slightly soluble in water (0.03 wt-% at 25° C.). Alkali metal iodides, which combine with iodine to form triiodide ($I_3^-$), increase that solubility. Molecular iodine, however, can be very irritating at higher concentrations. For example, Lugol's solution (5% elemental iodine and 10% potassium iodide) and tincture of iodine (45% aqueous ethanol with 2% elemental iodine and 2.4% sodium iodide) have both been well documented to be quite irritating to the skin.

Many references have described the preparation of "iodophors," which are complexes of elemental iodine or triiodide with certain carriers. These iodophors function to not only increase the iodine solubility but to reduce the level of free molecular iodine in solution and to provide a type of sustained release reservoir of elemental iodine. Iodophors are known using carriers of polymers such as polyvinylpyrrolidone, copolymers of N-vinyl lactams with other unsaturated monomers such as, but not limited to, acrylates and acrylamides, various polyether glycols including polyether-containing surfactants such as nonylphenolethoxylates and the like, polyvinyl alcohols, polycarboxylic acids such as polyacrylic acid, polyacrylamides, polysaccharides such as dextrose, and the like, and combinations thereof. A suitable group of iodophors includes polymers such as a polyvinylpyrrolidone (PVP), a copolymer of N-vinyl lactam, a polyether glycol (PEG), a polyvinyl alcohol, a polyacrylamide, a polysaccharide, and combinations thereof. Also reported in U.S. Pat. No. 4,597,975 (Woodward et al.) are protonated amine oxide surfactant-triiodide complexes that are also suitable iodophors for use in the present invention. Various combinations of iodophors can be used in the compositions of the present invention.

A preferred iodophor is povidone-iodine. Particularly suitable povidone-iodine can be obtained commercially as povidone-iodine USP, which is believed to be a complex of K30 polyvinylpyrrolidone, iodine, and iodide wherein the available iodine is present at 9 wt-% to 12 wt-%.

Preferably, the iodophor is present in the ready to use compositions at a concentration of at least 1 percent by weight (wt-%), preferably at least 2.5 wt-%, and more preferably at least 4 wt-%, and most preferably at least 5 wt-%, based on the total weight of the antiseptic composition. To prevent the dried composition from becoming excessively water soluble and/or to control irritation, iodine toxicity, and poor taste, the concentration of iodophor in the use composition is preferably present at not more than 15 wt-%, and more preferably not more than 10 wt-%, based on the total weight of the antiseptic composition.

Since iodophors may vary in the amount of available iodine it is usually more convenient to describe the concentration in terms of the available iodine level. In the present invention, whether from iodine or an iodophor or a combination thereof, the available iodine concentration is preferably at least 0.1 wt %, more preferably at least 0.2 wt-%, even more preferably at least 0.25 wt-%, and even more preferably at least 0.4 wt-%, based on the total weight of the ready to use antiseptic composition. Even more preferably, the compositions contain at least 0.50 wt-% available iodine, based on the total weight of the ready to use antiseptic composition. Concentrations of available iodine below 0.1 wt-% may not be sufficiently bactericidal. The available iodine is preferably present at not more than 2 wt-%, more preferably no more than 1.5 wt-%, and even more preferably not more than 1 wt-%, based on the total weight of the ready to use antiseptic composition. Concentrations of available iodine above 2 wt-% may be too irritating to wound and mucosal tissue and skin. The available iodine for most compositions may be determined by following the method in the United States Pharmacopeia Official Monographs for Povidone-Iodine, Assay for Available Iodine. Certain formulations may contain components that can interact with the method such as other anionic species. For this reason, the proper standards must be run to ensure accuracy, and solvent systems or reagents may need to be changed to ensure accuracy. One skilled in the art would appreciate these considerations.

Hydroxycarboxylic Acid Buffer

The compositions of the present invention are preferably buffered to prevent pH drift during storage. For example, it is well known that for iodine-containing systems it is desired to maintain the pH at generally 2 to 6, and preferably at 3 to 5. As the pH is raised above 6, the iodine can be rapidly converted to iodide, thus inactivating the antimicrobial effectiveness. The composition may become irritating if the pH falls below 2. In the compositions of the present invention, the pH is typically adjusted to 3.0 to 4.5.

While conventional compositions have included a variety of organic and inorganic buffers at concentrations of 0.1 wt-% to 2 wt-%, compositions of the present invention include certain hydroxycarboxylic acid buffers that can be used in much higher buffer concentrations. Preferably, a hydroxycarboxylic acid buffer is present in an amount of greater than 1 wt-%, more preferably greater than 2.5 wt-%, even more preferably greater than 3 wt-%, and even more preferably greater than 5 wt-%, and most preferably greater than 6 wt-%, based on the total weight of the antiseptic composition.

Surprisingly, these compositions (i.e., with a pH preferably adjusted to 3.0 to 4.5, and a relatively high hydroxycarboxylic acid buffer concentration—greater than 1 wt-%, and more preferably greater than 6 wt-%) are substantially nonirritating to tissue (e.g., skin and mucosal tissue), as indicated by studies conducted by instilling aliquots (of use concentrations) into rabbit eyes. Preferred compositions when tested according to the Rabbit Eye Irritation Test disclosed in U.S. Pat. No. 7,147,873 produce very little, if any, corneal opacity, with substantially complete return to normal (i.e., clear or having a Draize score of zero) in no greater than 96 hours, and preferably no greater than 72 hours. This indicates that the compositions would be very gentle for use on skin and mucosal tissue.

This level of buffer is particularly desirable for antiseptic compositions that include povidone-iodine (particularly povidone-iodine USP) as the antimicrobial agent. In these systems the level of rapid microbial kill increases significantly and for some systems in a linear fashion with the molar concentration of the hydroxycarboxylic acid.

Preferred hydroxycarboxylic acid buffers include one or more compounds disclosed in U.S. Pat. No. 7,147,873 (Scholz et al.) and are represented by the formula: $R^1(CR^2OH)_n(CH_2)_mCOOH$ wherein: $R^1$ and $R^2$ are each independently H or a (C1-C8)alkyl group (saturated straight, branched, or cyclic group), a (C6-C12)aryl, or a (C6-C12) aralkyl or alkaryl group (saturated straight, branched, or cyclic alkyl group), wherein $R^1$ and $R^2$ may be optionally substituted with one or more carboxylic acid groups; m=0 or 1; and n=1-3, preferably, n=1-2.

It is particularly desirable that the buffers and other excipients that contain hydrocarbon groups are saturated or contain low levels of unsaturation to prevent iodine addition, which may deplete the iodine in the composition and/or produce toxic species. Preferably, the level of unsaturation in the composition is no greater than 50 milliequivalents per liter (meq/L), more preferably, no greater than 5 meq/L, and most preferably, no greater than 0.5 meq/L unsaturation.

The hydroxycarboxylic acid buffers of the present invention include preferably beta- and alpha-hydroxy acids (BHAs, AHAs, respectively, collectively referred to as hydroxy acids (HAs)), salts thereof, lactones thereof, and/or derivatives thereof (preferably, alpha-hydroxy acids are used). These may include mono-, di-, and tri-functional carboxylic acids. Particularly preferred are HAs having 1 or 2 hydroxyl groups and 1 or 2 carboxylic acid groups. Suitable HAs include, but are not limited to, lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof). Preferred HAs include lactic acid, malic acid, and citric acid. These acids may be in D, L, or DL form and may be present as free acid, lactone, or salts thereof. Other suitable HAs are described in U.S. Pat. No. 5,665,776 (Yu et al.). The preferred HAs for use with iodine, and in particular with povidone-iodine, are lactic and malic acid and combinations thereof. Various combinations of hydroxycarboxylic acids can be used if desired.

A hydroxycarboxylic acid buffer is preferably present in a molar concentration of at least 0.1 molar, more preferably at least 0.3 molar, more preferably at least 0.45 molar, and even more preferably at least 0.6 molar. For formulations where very rapid microbial kill on skin is desired the hydroxycarboxylic acid concentration is in excess of 0.7 molar.

Without wishing to be bound by theory, the antimicrobial efficacy of antimicrobial compositions containing povidone-iodine is directly related to the molar concentration of hydroxycarboxylic acid buffer. With sufficiently high levels of hydroxycarboxylic acid buffer, compositions containing povidone-iodine are able to reduce the normal skin flora on a dry human skin site (typically, the back or abdomen) by an average of greater than or equal to 2 logs in only 2 minutes following a 30-second scrub, and preferably following a simple painting application (no scrubbing) where the site is painted 3 times when tested according to ASTM testing method E1173-93.

Typically, the concentration of hydroxycarboxylic acid buffer in weight percent of the ready to use composition (i.e., a composition that need not undergo additional dilution before application to tissue) is at least about 2% by weight, preferably at least about 5 wt-% and often at least about 7 wt-%, based on the weight of the ready to use composition. The concentration of hydroxycarboxylic acid buffer is preferably no greater than about 15 wt-%, more preferably no greater than about 10 wt-%, based on the weight of the ready to use composition. It may also be convenient in some applications to supply concentrates that have much higher concentration of hydroxycarboxylic acid buffer but when diluted to the use concentration fall within the specified ranges.

Preferably, the ratio of hydroxycarboxylic acid ("HA") buffer (free acids, as well as lactones thereof, salts thereof, or derivatives thereof) to antimicrobial agent is at least about 4.0 grams HA buffer per gram available iodine, more preferably, at least about 6.5 grams HA buffer per gram available iodine, and most preferably, at least about 9.0 grams HA buffer per gram available iodine.

Amine Oxide/Iodide Salt

Iodide salts and amine oxide surfactants separately have been reported to stabilize iodine-containing solutions. As shown in the Examples, however, certain hydroxycarboxylic acid-comprising iodine-containing formulations are not sufficiently stabilized toward available iodine loss by either sodium iodide or amine oxide surfactants alone (i.e., the loss of available iodine is not sufficiently prevented). Surprisingly, combinations of amine oxide sufactant(s) and iodide salt(s) stabilize the hydroxycarboxylic acid-comprising formulations of the present invention. Though certain preferred concentrations are disclosed herein, the amount of amine oxide and iodide salt that will iodine stabilize a hydroxyacid-comprising antiseptic iodine composition may vary for different compositions and packaging types.

Amine Oxide

Amine oxides have been reported to complex molecular iodine and/or triiodide, thus stabilizing some iodine solutions. The amine oxide may be a compound, oligomer, or polymer comprising one or more amine oxide groups or compound comprising a single amine oxide group. Suitable amine oxides are preferably acceptable for a topical pharmaceutical formulation, i.e., one that is not appreciably irritating or toxic to skin or mucosal tissue. Examples of particularly suitable amine oxides for use in the present invention are those having surface activity (surfactants) and are generally characterized as having at least one alkyl group having a weight average chain length of greater than 6 carbon atoms, preferably greater than 8 carbon atoms, and most preferably greater than 10 carbon atoms. Also included are amine oxides of aromatic tertiary amines and tertiary amines comprising an alkaryl group such as dimethylbenzylamine oxide. The trialkylamine oxides (e.g. lauryldimethylamine oxide) have at least one C6-C22 alkyl group wherein the alkyl group or groups can be optionally substituted in or on the chain by N, O, or S. The alkaryldialkyl amine oxides have at least one alkaryl group having at least 7 carbon atoms and alkyl groups of C1-C22 optionally substituted in or on the chain by N, O, or S. Particularly useful are myristamine oxides such as myristamidopropyldimethylamine oxide, lauramine oxides such as lauramidopropyldialkylamine oxide, dihydroxyethyldodecylamine oxide, and mixtures thereof. Additional amine oxides suitable for use in the compositions of the present invention include those commercially available under the trade designations AMMONYX LO, LMDO, and CO, which are lauryldimethylamine oxide, laurylamidopropyldimethylamine oxide, and cetyl amine oxide, all from Stepan Co. (Northfield, Ill.), as well as N-oxides of ethoxylated tertiary amines such as those having the structure $R_2$—N$(AO)_2$, R—N$(AO)_2$ or R—N(AO)—R'N$(AO)_2$ or R—N(AO)—R'N(AO) where AO=polyalklyene oxide having 1-100 moles of ethylene oxide or propylene oxide residues and R=C1-C22, preferably C8-C18 aliphatic hydrocarbon optionally substituted with N, O, or S. R' is a connecting group and is most preferably a C2-C10 alkylene group. Examples include Ethomeen and alkoxylated Duomeen tertiary amines available from Akzo Nobel, Additional examples of suitable tertiary amine oxides include: N,N-dimethyl benzylamine oxide; N-ethyl, N-lauryl benzylamine oxide; N-methyl N-ethyl benzylamine oxide; 4-alkyl pyridine N-oxide, 3-alkyl pyridine N-oxide, 2 alkyl pyridine N-oxide; alkyl pyrazine N-oxide; alkyl pyrazine N, N'-dioxide; N-alkyl piperidine N-oxide; N,N'-alkyl piperazine N-oxide; N,N' diakyl piperazine N,N'-dioxide; N-alkyl morpholine N-oxide; alkyl substituted quinoline N-oxide; N,N-dialkyl cyclohexylamine N-oxide; N,N-dialkylaniline N-oxide, and the like as well as mixtures thereof. Other suitable amine oxides may be found in U.S. Pat. No. 4,597,975 incorporated herein by reference.

In certain embodiments, the amine oxides in the antiseptic compositions are present in an amount such that the ratio of the total moles of amine oxide to total moles of available iodine is less than about 2. Preferably, the total amine oxide present in the ready to use compositions of the present invention is at least about 0.25 wt-% of the total weight of the antiseptic composition. More preferably, the total amine oxide present is at least about 0.5 wt-%. In certain embodiments, the total amine oxide present in the composition is no greater than about 2.0 wt-%, and more preferably no greater than about 1 wt-% of the total weight of the composition. Higher concentrations of amine oxides may cause some irritation or other discomfort when applied to skin or mucosal tissue.

Iodide Salt

The compositions of the present invention contain one or more iodide salts. Preferred iodide salts include sodium iodide (NaI), potassium iodide (KI), calcium iodide ($CaI_2$), and zinc iodide ($ZnI_2$) and combinations thereof. Preferably, the iodide salt is present at a total concentration of at least about 1.5 wt-% based on the total weight of the antiseptic composition. More preferably, the iodide salt is present in the antiseptic compositions at a total concentration of at least about 2.0 wt-% and even more preferably at least about 2.5 wt-%. In certain embodiments, the iodide salt is present in the antiseptic composition at a total concentration of no greater than about 10 wt-% and preferably no greater than about 5 wt-% based on the total weight of the antiseptic composition. Compositions including less than a total concentration of about 1.5 wt-% iodide salt may not be iodine stable. For example, commercially available povidone—iodine may contain as much as 0.6 wt-% iodide but is not alone sufficient for iodine stability in ready to use compositions containing elevated levels of hydroxycarboxylic acid.

Optional Monosaccharides and Sugar Alcohols

Suitable monosaccharides for use in the compositions described herein have the chemical formula $(CH_2O)_{n+m}$ with the chemical structure $H(CHOH)_nC=O(CHOH)_mH$. If n or m is zero, it is an aldehyde and is termed an aldose, otherwise it is a ketone and is termed a ketose. Monosaccharides contain either a ketone or aldehyde functional group, and hydroxyl groups on most or all of the non-carbonyl carbon atoms. The monosaccarides found most useful are 5 and 6 carbon atom (n+m=5 or 6) compounds. They may be found in the D or L form or a combination thereof. The most preferred monosaccharides are xylose, xylulose, lyxose, mannose, maltose, sorbose, erythrose, glucose (dextrose), fructose, galactose, and ribose The term "sugar alcohol" is understood to mean a monosaccharide or a disaccharide in which the aldehyde group of the first carbon atom is reduced to a primary alcohol. They include the following preferred sugar alcohols: xylitol, sorbitol, mannitol, maltitol, erythritol, lactitol and arabitol or combinations thereof. More preferred sugar alcohols are those derived from monosaccharides (i.e., alcohols of a monosaccharide) including xylitol, mannitol, or combinations thereof. A particularly preferred sugar alcohol is xylitol. As used herein, the term "alcohol of a monosaccharide" is understood to mean a monosaccharide in which the aldehyde group of the first carbon atom is reduced to a primary alcohol.

These monosaccharides and/or sugar alcohols have been found to further increase the efficacy (i.e., speed and/or extent of bacterial kill) of iodine containing compositions. (See e.g., U.S. Application Publication No. 2009/0169647 (Scholz)).

The monosaccharides and/or sugar alcohols are preferably present in a concentration of at least 0.25 wt-%, more preferably at least 0.5 wt-%, even more preferably at least 1 wt-%, even more preferably at least 2 wt-%, even more preferably at least 4 wt-%, and even more preferably at least 5 wt-%, based on the total weight of the composition. The concentration is typically adjusted to ensure improved antimicrobial performance and/or to improve the taste of the composition if it is applied to the oral cavity, esophageal cavity, nasal passages, or anterior nares. The upper limit may be determined by the solubility limit of the monosaccharide and/or sugar alcohol. In preferred compositions the monosaccharide and/or sugar alcohol is completely soluble with no solid dispersed therein. Such formulations are easier to maintain physical stability, i.e., to prevent settling and non-uniformity. Stability should be examined 2-4 weeks after manufacture when stored at room temperature. Preferred formulations do not exhibit any solid monosaccharide and/or sugar alcohol after standing. For example, it has been found that in PEG 400 xylitol is initially in solution when heated to 70° C. Upon standing for 2 weeks, however, some of the compositions showed separation of solid xylitol. Addition of 5-20 wt-% water was found to keep the xylitol stable in solution (depending on the amount of xylitol used).

Optional Additional Surfactants

For effective kill on skin and mucosal tissue the compositions of the present invention may include one or more surfactants. Necessarily, the surfactants must be compatible with the antimicrobial agent, the hydroxycarboxylic acid buffer, and the amine oxide/iodide salt combination, as well as any other optional ingredients, such as monosaccharides and/or sugar alcohols. It may be particularly desirable when formulating with a film-forming polymer to include one or more surfactants to enhance solubility and stability of the polymer in the composition. In addition, surfactants help the compositions to wet the skin and ensure a smooth uniform coating. It is particularly desirable to provide a coating (preferably, substantive) that has complete coverage to ensure easy error-free application. On tissues that are hard to visualize, such as most mucosal surfaces, it is desirable to use surfactants to help wetting and to ensure the antimicrobial agent will be distributed by diffusion and or capillary action across the tissue. On skin it is preferred that a thin relatively uniform coating is applied that will dry rapidly. In addition, certain surfactants may increase the antimicrobial activity.

If used, one or more surfactants are generally added to the ready to use antiseptic compositions of the present invention in an amount of at least about 0.25 wt-% and preferably at least about 0.5 wt-%, based on the total weight of the composition. Preferably, one or more surfactants are generally added to the antiseptic compositions of the present invention in an amount of no greater than about 10 wt-%, more preferably no greater than about 7 wt-%, even more preferably no greater than about 5 wt-%, and most preferably no greater than about 3 wt-%, based on the total weight of the composition. Too little surfactant may result in an unstable composition (especially upon exposure to elevated temperatures) and/or reduced antimicrobial efficacy on tissue. Too much surfactant can undermine the substantivity of the dried composition on skin and contribute to tissue irritation. For this reason, the surfactant level is generally chosen as slightly above the minimum level of total surfactant required to ensure stability at 50° C.

Furthermore, it is preferred to use surfactants having low inorganic salt impurities such as sodium chloride, sodium sulfate, etc. Preferably, such salt content should be sufficiently low such that a 20% solution of the surfactant in water has a conductivity of less than 100 microohms per centimeter (microohms/cm), more preferably less than 85 microohms/cm, and most preferably less than 75 microohms/cm.

The following types of surfactants can be used if desired:

a. Nonionic Surfactants. Useful surfactants include nonionic surfactants. It has been found that polyalkoxylated, and in particular polyethoxylated, nonionic surfactants can stabilize film-forming polymers in aqueous solutions particularly well. In general, useful polyalkoxylated nonionic surfactants preferably have a hydrophile/lipophile balance (HLB) of at least 14, and more preferably at least 16. Useful polyalkoxylated nonionic surfactants preferably have an HLB of no greater than 19. When using combinations of nonionic surfactants a weight average HLB is used to determine the HLB of the nonionic surfactant system. As used herein, the HLB is defined as one-fifth the weight percentage of ethylene oxide segments in the surfactant molecule.

Surfactants of the nonionic type that have been particularly useful include:

1. Polyethylene oxide extended sorbitan monoalkylates (i.e., POLYSORBATES). In particular, a Polysorbate 20 commercially available as NIKKOL TL-10 (from Barret Products) is very effective.
2. Polyalkoxylated alkanols. Surfactants such as those commercially available under the trade designation BRIJ from ICI Specialty Chemicals, Wilmington, Del., having an HLB of at least 14 have proven useful. In particular, BRIJ 78 and BRIJ 700, which are stearyl alcohol ethoxylates having 20 and 100 moles of polyethylene oxide, respectively, have proven very useful. Also useful is a ceteareth 55, which is commercially available under the trade designation PLURAFAC A-39 from BASF Corp., Performance Chemicals Div., Mt. Olive, N.J.
3. Polyalkoxylated alkylphenols. Useful surfactants of this type include polyethoxylated octyl or nonyl phenols having HLB values of at least 14, which are commercially available under the trade designations ICONOL and TRITON, from BASF Corp., Performance Chemicals Div., Mt. Olive, N.J. and Union Carbide Corp., Danbury, Conn., respectively. Examples include TRITON X100 (an octyl phenol having 15 moles of ethylene oxide available from Union Carbide Corp., Danbury, Conn.) and ICONOL NP70 and NP40 (nonyl phenol having 40 and 70 moles of ethylene oxide units, respectively, available from BASF Corp., Performance Chemicals Div., Mt. Olive, N.J.). Sulfated and phosphated derivatives of these surfactants are also useful. Examples of such derivatives include ammonium nonoxynol-4-sulfate, which is commercially available under the trade designation RHODAPEX CO-436 from Rhodia, Dayton, N.J.
4. Polaxamers. Surfactants based on block copolymers of ethylene oxide (EO) and propylene oxide (PO) have been shown to be effective at stabilizing film-forming polymers and provide good wetting. Both EO-PO-EO blocks and PO-EO-PO blocks are expected to work well as long as the HLB is at least 14, and preferably at least 16. Such surfactants are commercially available under the trade designations PLURONIC and TETRONIC from BASF Corp., Performance Chemicals Div., Mt. Olive, N.J. It is noted that the PLURONIC surfactants from BASF have reported HLB values that are calculated differently than described above. In such situation, the HLB values reported by BASF should be used. For example, preferred PLURONIC surfactants are L-64 and F-127, which have HLBs of 15 and 22, respectively. Although the PLURONIC surfactants are quite effective at stabilizing the compositions of the present invention and are quite effective with iodine as the active agent, they may reduce the antimicrobial activity of compositions using povidone-iodine as the active agent.
5. Polyalkoxylated esters. Polyalkoxylated glycols such as ethylene glycol, propylene glycol, glycerol, and the like may be partially or completely esterified, i.e., one or more alcohols may be esterified, with a (C8-C22)alkyl carboxylic acid. Such polyethoxylated esters having an HLB of at least 14, and preferably at least 16, are suitable for use in compositions of the present invention.
6. Alkyl Polyglucosides. Alkyl polyglucosides, such as those described in U.S. Pat. No. 5,951,993 (Scholz et al.), starting at column 9, line 44, are compatible with film-forming polymers and may contribute to polymer stability. Examples include glucopon 425, which has a (C8-C16)alkyl chain length with an average chain length of 10.3 carbons and 1-4 glucose units.

b. Zwitterionic Surfactants. Surfactants of the zwitterionic type include surfactants having tertiary amine groups which may be protonated as well as quaternary amine-containing zwitterionic surfactants. Those that have been particularly useful include:

1. Ammonium Carboxylate Zwitterionics. This class of surfactants can be represented by the following formula:

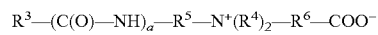

wherein: $a=0$ or 1; $R^3$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^3$ may be optionally substituted with one or more N, O, or S atoms, or one or more hydroxyl, carboxyl, amide, or amine groups; $R^4$ is H or a (C1-C8)alkyl group (saturated straight, branched, or cyclic group), wherein $R^4$ may be optionally substituted with one or more N, O, or S atoms, or one or more hydroxyl, carboxyl, amine groups, a (C6-C9)aryl group, or a (C6-C9)aralkyl or alkaryl group; and $R^5$ and $R^6$ are each independently a (C1-C10)alkylene group that may be the same or different and may be optionally substituted with one or more N, O, or S atoms, or one or more hydroxyl or amine groups.

More preferably, in the formula above for ammonium carboxylate zwitterionics, $R^3$ is a (C1-C16)alkyl group, $R^4$ is a (C1-C2)alkyl group preferably substituted with a methyl or benzyl group and most preferably with a methyl group. When $R^4$ is H it is understood that the surfactant at higher pH values could exist as a tertiary amine with a cationic counterion such as Na, K, Li, or a quaternary amine group.

Examples of such zwitterionic surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Zwitterionics. This class of zwitterionic surfactants are often referred to as "sultaines" or "sulfobetaines" and can be represented by the following formula

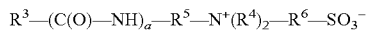

wherein $R^3$-$R^6$ and "a" are defined as above for ammonium carboxylate zwitterionics. Examples include cocamidopropylhydroxysultaine and lauramidopropylhydroxy sultaine (commercially available as MACKAM 50-SB from McIntyre Group Ltd.).

3. Phospholipid Zwitterionics. These surfactants are characterized as having at lease one anionic phosphate group, one cationic ammonium group (either protonated or quaternary), and at least one alkyl, alkenyl, aralkyl, or aralkenyl group of at least 8 carbon atoms. Many surfactants of this class of surfactants can be represented by the following formula:

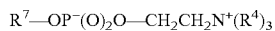

wherein $R^4$ is defined above for ammonium carboxylate zwitterionics and $R^7$ is $R^3$ (as defined above for ammonium carboxylate zwitterionics) with the proviso that $R^7$ also may comprise multiple $R^3$ groups as would be the case if $R^7$ were a glycerol ester derivative as, for example, in phosphatidylcholine. Examples include lecithins, phosphatidylcholine and phosphatidylethanol amine. The so called "reverse phospholipids" which possess a quaternary ammonium group in the chain and a terminal phosphate group are also possible such as those sold by Uniqema/Croda under the tradename Arlasilk Phospholipid CDM (coco PG-dimonium chloride phosphate), Arlasilk Phospholipid EFA (Linoleamidopropyl PG-Dimonium Chloride Phosphate), and the like.

c. Anionic Surfactants. Surfactants of the Anionic Type that have been Particularly Suitable Include:

1. Sulfonates and Sulfates. Suitable anionic surfactants include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates and the like. Many of these can be represented by the formulas:

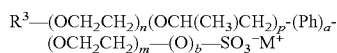

and

wherein: a and b=0 or 1; n, p, m=0-100 (preferably 0-40, and more preferably 0-20); $R^3$ is defined as above for zwitterionics; $R^7$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as Na, K, Li, ammonium, a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^3$ comprises an alkylamide group such as $R^8$—C(O)N(CH$_3$)CH$_2$CH$_2$— as well as ester groups such as —OC(O)—CH$_2$— wherein $R^8$ is a (C8-C22)alkyl group (saturated branched, straight, or cyclic group).

Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo (C12-16)ester and disodium 2-sulfo(C12-C16)fatty acid available from Stepan Company under the trade designation ALPHASTE PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company.

2. Phosphates and Phosponates. Suitable anionic surfactants also include phosphates such as alkyl phosphates, alkylether phosphates, aralkylphosphates, glycerol ester phosphates, and aralkylether phosphates. Many may be represented by the formula:

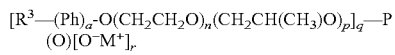

where: Ph, $R^3$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement.

Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J.

Combinations of various surfactants can be used if desired. For example, nonionic surfactants in combination with certain anionic surfactants or zwitterionic surfactants described above can be used for certain advantage. For example, one preferred surfactant system is based on a combination of a polysorbate and a polyethoxylated alkyl alcohol (POLYSORBATE 20+steareth-100).

Certain suitable zwitterionic surfactants include sultaines, betaines, phospholipids, or combinations thereof. In preferred embodiments, the zwitterionic surfactant is a sultaine, a phospholipids, or a combination thereof.

Certain suitable anionic surfactants include a polyalkoxylate group. These include the sulfonates, sulfates, phosphates, and phosphonates. Various combinations of these can be used if desired.

For certain embodiments, it is desirable to select one or more surfactants that associate or potentially associate with other components in the composition after dry down may be better tolerated. For example, certain anionic surfactants such as methyl-2-sulfoalkyl esters (e.g., sodium methyl-2-sulfo (C12-16) ester and disodium 2-sulfo(C12-C16)fatty acid available from Stepan Company under the trade designation ALPHASTEP PC-48) in combination with polyamine oxide film-forming polymers appear to increase the substantivity of a dried film of the antiseptic composition and adhesion of PSA-coated products. Certain of the sulfate and sulfonate containing surfactants also appear to significantly reduce dry times. The mechanism for this is not clear. While not intending to be bound by theory these surfactants may associate with cationic amine groups on film-forming polymers forming a more hydrophobic complex during dry down. Sulfates and sulfonates, phosphates and phosphonates, as well as the sulfobetaine type surfactants have been shown to reduce the dry time significantly.

Vehicles

Suitable vehicles include injectable-grade water, i.e., USP grade "water for injection, and other purified water, such as distilled and deionized water. Another preferred vehicle is polyethylene glycol (PEG), preferably having a weight average molecular weight of less than 1500 daltons, more preferably less than 1000 daltons, and even more preferably less than 600 daltons. It is recognized that these materials are comprised of a distribution of molecular weights. These materials have the following chemical structure: $H-(OCH_2CH_2)_n-OH$. Preferably these PEGs meet USP or NF specifications. Some sugar alcohols and monosaccharides may not be soluble in neat PEG. For example, xylitol at 5 wt-% will dissolve in PEG 400 if heated but this will phase out over a few days to weeks time. Thus, PEG-containing vehicles may need additional components to help the solubility such as water, another glycol, a surfactant, or a combination thereof. A preferred embodiment of the vehicle includes PEG and water.

Particularly preferred antiseptic compositions for use on mucosal tissue include purified water and are substantially free (i.e., less than 10 wt-%) of volatile organic solvents (i.e., those having a closed-cap flash point of greater than 140° F. (60° C.)), such as acetone, lower alcohols, alkanes, volatile silicones, etc.

Aqueous formulations are preferred since these formulations are gentle to both skin and mucosal tissue and may even be suitable for use on open wounds as a wound cleanser. Furthermore, compositions containing organic solvents also may be flammable, which is typically a consideration in shipping and handling the product.

Preferred compositions of the present invention for use on mucosal tissue (oral, esophageal, nasal, anterior nares, vaginal, and wound) include less than 5 wt-% volatile organic solvents, and more preferably less than 3 wt-% volatile organic solvents, based on the total weight of the composition. Lower levels of volatiles are particularly important in nasal and oral applications where the volatiles could be inhaled. These preferred aqueous compositions typically are nonflammable, having a closed-cup flash point of greater than 140° F. (60° C.). The addition of lower alcohols (C1-C4) at less than 4 wt-% may improve wetting of the compositions and yet maintain a flashpoint above 140° F. (60° C.). Flashpoint is measured according to test method ASTM D3278-96.

For applications to intact skin, however, it may be desirable to include a lower alcohol such as ethanol, isopropanol, or n-propanol. These alcohols are well known to contribute to rapid microbial kill. For these applications the alcohol to water ratio is preferably at least 60:40, and more preferably at least 70:30, by weight. Addition of alcohol in these high concentrations will also decrease the dry time of the composition.

When a lower alcohol is used, incorporation of surfactants (as discussed in greater detail above) may or may not be necessary. In most cases reduction or elimination of the surfactant may allow for better adhesion of PSA-coated products over the dried film.

For embodiments of the composition including a monosaccharide and/or sugar alcohol, suitable vehicles include vehicles in which a monosaccharide and/or sugar alcohol is soluble, forming a clear and transparent solution having a percent transmission at 550 nanometers (nm) of greater than 85% in a cuvette with a path length of 1 centimeter (cm) at room temperature. The test solution is the composition less the antimicrobial agent and any thickener or film-forming polymer as well as the surfactant and any other insoluble species such as fillers or other particulates. Preferred compositions are stable and still clear after standing for 2 weeks at 23C. Thus, to ensure solubility of the monosaccharide and/or sugar alcohol the vehicles in these embodiments generally include water, acetone, an alcohol (particularly a (C1-C4) alcohol (i.e., a lower alcohol) such as ethanol, 2-propanol, and n-propanol), or mixtures thereof. Preferably the sugar or sugar alcohol are added at less than the solubility limit.

Vehicles can include one or more humectants such as glycols, particularly polyalkylene glycols (e.g., polyethylene glycol, polypropylene glycol). In certain embodiments, the humectants (particularly polyalkylene glycols) are water-soluble, which means that when added to deionized water at 5% and mixed very well for 2 hours the percent transmission at 550 nm in a 1-cm path length cell is greater than 90%. In certain embodiments, the polyalkylene glycols have a molecular weight of less than 2500 daltons, preferably less than 1500 daltons, and more preferably less than 1000 daltons. Nonlimiting examples of preferred humectant-type glycol (polyols) include glycerol, polyglycerin, 1,3- and 1,4-butylene glycol, propylene glycol, dipropylene glycol, polypropylene glycol, polyethylene glycol, sorbitol, pantothenol, gluconic acid salts, and the like, including polyethoxylated derivatives thereof.

Optional Thickening Agents and Film-Forming Polymers

It is often desirable to add one or more thickening agents, particularly polymeric thickeners (which may be film-forming polymers), and/or film-forming polymers, to the antiseptic compositions to improve substantivity (e.g., resistance to wash off by blood and body fluid exposure), improve adhesion of PSA-coated products, increase viscosity to prevent dripping, etc., reduce the tack of the compositions, and/or reduce the loss of available iodine during storage. Preferred polymeric thickeners and/or film-forming polymers of the antiseptic compositions of the present invention are substantive and resist removal by prolonged exposure to fluids such as water, saline, and body fluids, yet can be easily and gently removed without the need for organic solvents.

Certain skin antiseptic compositions of the present invention resist removal particularly well after they are dry. These compositions generally have lower viscosity (e.g., less than 1000 cps), and preferably greater than 10 cps, and have polymers with generally lower molecular weight (e.g., less than 200,000 daltons).

Antiseptic compositions for use on wound and mucosal tissues such as in the nose and anterior nares, however, have a higher viscosity in order to retain the composition on the tissue (which is often wet) longer and to prevent dripping and mess. These compositions preferably have a viscosity in excess of 100 cps, more preferably in excess of 500 cps, even more preferably in excess of 1000 cps, even more preferably in excess of 2000 cps, and even more preferably in excess of 5000 cps, and even more preferably in excess of 8000 cps. These compositions may be thickened with one or more of the following:

a. Polymeric thickeners
    b. Hydrophobically modified polymeric thickeners
    c. Polymer/surfactant combinations
    d. Emulsifiers (including waxes)
    e. Inorganic colloidal thickeners Polymeric Thickeners for Topical Skin Antiseptics (e.g., Pre-surgical and IV Preps):

Preferred polymeric thickeners (which may be film-formers) have both hydrophilic and hydrophobic moieties. Particularly preferred polymeric thickeners include relatively high levels of total hydrophobic monomers. The preferred polymers are relatively hydrophobic to provide good substantivity and prolonged adhesion of PSA-coated products. Particularly preferred polymers are formed using a hydrophobic monomer level of at least 50 wt-%, and often as high as 80 wt-%, based on the total weight of the polymerizable composition (and preferably, based on the total weight of the polymer). Various combinations of hydrophobic monomers can be used if desired.

Examples of suitable hydrophobic and hydrophilic monomers are described in U.S. Pat. No. 6,838,078.

The polymeric thickeners (which may be film-forming polymers) can be nonionic, anionic, cationic, or zwitterionic. They may also have pressure sensitive adhesive properties. These include both synthetic and natural polymers as well as derivatives of natural polymers. Preferred polymers are cationic (particularly film-forming polymers).

Surprisingly, the solubility and stability of cationic polymeric thickeners are not affected detrimentally by the presence of multifunctional carboxylic acid containing hydroxyacids such as citric acid, malic acid, tartaric acid, and the like. This is particularly surprising since it would be expected that adding these acids into compositions containing cationic polymers at very high concentrations would result in precipitation of the polymer due, for example, to ionic crosslinking.

In certain embodiments, preferred polymeric thickeners are cationic polymers, particularly those that include side-chain functional amine groups, which can be film-forming polymers. Examples of such groups include protonated tertiary amines, quaternary amines, amine oxides, and combinations thereof. Preferred such polymers are described in U.S. Pat. No. 6,838,078.

In certain embodiments, preferred polymeric thickeners are vinyl polymers prepared from amine group-containing monomers. Preferably, the vinyl polymers have a Tg of at least 30° C., and more preferably at least 50° C. One method of measuring the Tg of a polymer may involve the utilization of a Differential Scanning Calorimeter (DSC, e.g., the PYRIS 7-Series Thermal Analyzer, Perkin-Elmer, Shelton, Conn.) in the range of −100° C. to +100° C. at a rate of 20° C. per minute.

For certain preferred polymeric thickeners, the amine group-containing monomers can be used to prepare the polymers in an amount of at least 15 wt-%, more preferably at least 20 wt-%, even more preferably at least 25 wt-%, and most preferably at least 30 wt-%, based on the total weight of the polymerizable composition (and preferably, based on the total weight of the polymer). The amine group-containing monomers used to prepare the polymers are typically used in an amount of no greater than 70 wt-%, preferably no more greater than 65 wt-%, more preferably no greater than 60 wt-%, and most preferably no greater than 55 wt-%, based on the total weight of the polymerizable composition (and preferably, based on the total weight of the polymer).

The equivalent weight of the amine group contained in the polymer is preferably at least 300, more preferably at least 350, even more preferably at least 400, and most preferably at least 500, grams polymer per equivalent of amine group. The equivalent weight of the amine group contained in the polymer is preferably no greater than 3000, more preferably no greater than 1500, even more preferably no greater than 1200, and most preferably no greater than 950, grams polymer per equivalent of amine group.

Examples of polymeric thickeners that are film-forming polymers and that are PSAs at room temperature include those based on side-chain functional amine group monomers in combination with long chain alkyl acrylic polymers and optionally other hydrophilic monomers. For example, a particularly effective polymer that is a PSA includes 80% 2-ethylhexylacrylate and 20% trimethylaminoethyl methacrylate chloride, based on the total weight of the polymerizable composition (and preferably, based on the total weight of the polymer). Another PSA polymer in this class includes 75% 2-ethylhexyl acrylate, 25% trimethylaminoethyl methacrylate chloride, and 5% of a methoxy polyethylene glycol (9 ethyleneoxy units) monoacrylate, which is commercially available from Shin-Nakamura Chemicals, Wakayama City, Japan under the trade designation AM-90G.

For certain embodiments, preferably the viscosity of a composition of the present invention intended for use on topical skin is no greater than 1000 cps (and is preferably greater than 10 cps) when measured at 23° C. using a Brookfield LVT viscometer as described in the Examples. Therefore, useful polymers (preferably film-forming polymers) in the compositions of the present invention preferably have an inherent viscosity of no greater than 0.75, and more preferably no greater than 0.5 as measured in tetrahydrofuran according to the method in U.S. Pat. No. 7,147,873. In order to ensure sufficient substantivity, however, the inherent viscosity of the polymer (preferably film-forming polymer) is preferably at least 0.1, as measured in tetrahydrofuran according to the method in U.S. Pat. No. 7,147,873.

The molecular weight of the polymers is also preferably kept low in order to maintain a low viscosity composition for applications to tissue where the composition will dry such as skin. Preferably, the molecular weight of the polymers is generally no greater than 350,000 daltons, more preferably no greater than 250,000 daltons, even more preferably no greater than 150,000 daltons, and most preferably no greater than 100,000 daltons.

In certain embodiments, one or more polymeric thickeners and/or film-forming polymers (preferably substantive film-forming polymeric thickeners), are present in the antiseptic composition in a total amount of at least 2 wt-%, preferably at least 3 wt-%, and more preferably at least 5 wt-%, based on the total weight of antiseptic composition. In certain embodiments, one or more polymeric thickeners and/or film-forming polymers (preferably substantive film-forming polymeric thickeners), are present in the antiseptic composition in a total amount of no greater than 10 wt-%, and more preferably no greater than 8 wt-%, based on the total weight of antiseptic composition. The optional one or more polymeric thickeners and/or film-forming polymers (preferably substantive film-forming polymeric thickeners) are preferably present in an amount to provide a substantive composition.

Higher concentrations of film-forming polymers appear to promote adhesion of PSA-coated products. In certain compositions, however, higher concentrations may not be possible due to instability especially when exposed to temperatures above 50° C.

Preferably, in order to ensure adequate substantivity the weight ratio of film-forming polymer to hydroxycarboxylic acid is at least 0.25:1, preferably at least 0.35:1, more preferably at least 0.5:1, and most preferably at least 0.70:1.

Thickening of Mucosal and Wound Tissue Antiseptic Compositions:

As briefly described above, compositions for use on moist tissue, such as most mucosal and wound tissue, preferably are formulated to have a higher viscosity. These compositions may not dry out upon application and therefore, use of higher viscosity compositions may help to retain the composition on the tissue for longer periods of time. For example, when used in the nasal passages, the nasal cilia will try to flush the composition out of the nasal passages and down the throat. Similarly, when used in the oral cavity or esophageal cavity oral secretions will tend to flush the composition down the throat. Thus, it is advantageous to thicken these compositions in order to retain the antiseptic on the tissue for prolonged periods of time to ensure adequate antisepsis. These compositions may be thickened by means known in the art and in particular by use of one or more of the following: polymeric thickeners, inorganic colloidal thickeners, hydrophobically modified polymeric thickeners, polymer/surfactant combinations, emulsifiers, and combinations thereof.

Suitable polymeric thickeners are numerous and include nonionic, cationic, zwitterionic, and anionic natural gums and modified natural gums. These include those that can impart a gel-like viscosity to the composition, such as water-soluble or colloidally water-soluble polymers like cellulose ethers (e.g., methylcellulose, hydroxybutyl methylcellulose, hydroxypropylcellulose, hydroxypropyl methylcellulose, hydroxyethyl ethylcellulose and hydroxyethylcellulose), guar gum, starch and starch derivatives, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, as well as derivatives thereof. Cationic derivatives of cellulose and guar are particular preferred.

Useful herein are vinyl polymers such as polyvinyl alcohol, polyvinyl pyrrolidone, linear and crosslinked acrylic acid polymers such as those with the CTFA name CARBOMER, cationic polymers such as polyquaterium 4, 10, 24, 32, and 37 and other polymeric thickening agents disclosed in U.S. Pat. No. 6,582,711, polyacrylamide, acrylamide copolymers, polyethyleneimine.

Cationic natural polymer derivatives can be useful thickening agents for compositions of the present invention. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquaternium-4. A particularly suitable type of cationic polysaccharide polymer that can be used is a cationic guar gum derivative, such as guar hydroxypropyltrimonium chloride (commercially available from Rhone-Poulenc under the trade designation JAGUAR).

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

Soluble polymers, particularly cationic synthetic polymers can also be useful thickening agents. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 150,000 daltons, and more preferably at least 250,000 daltons and most preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably, the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomer, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquaternium-16. This material is commercially available from BASF Wyandotte Corp. (Parsippany, N.J.) under the LUVIQUAT tradename (e.g., LUVIQUAT FC 370); copolymers of 1-vinyl-2-pyrrolidine and dimethylaminoethyl methacrylate, referred to in the industry (CTFA) as Polyquaternium-11. This material is available commercially from Gaf Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Preferred natural or modified natural gums are cationic or zwitterionic. A particularly preferred polymer is available as CELQUAT SC230M (polyquaternium 10) available from National Starch Personal Care, Bridgewater, N.J.

Alternatively, crosslinked cationic polymers may be used such as those disclosed in U.S. Pat. No. 6,582,711.

Inorganic water-insoluble, but perhaps swellable, materials can be useful thickening agents for compositions of the present invention. These include, but are not limited to, bentonite, aluminum magnesium silicate, laponite, hectonite, fumed silica, precipitated silica, silica sols and other silica particulate as well as anhydrous silicic acid, and the like.

Hydrophobically modified polymeric thickeners can be useful thickening agents for compositions of the present invention. These are, in general, polymers comprising at least one C8 or longer alkyl or alkenyl group. These polymers tend to associate in solution and are often referred to as associative polymers. Associative polymers can be used in the thickening system of the compositions of the present invention. It is believed that such polymers thicken as a result of hydrophobic or Van der Waals association of hydrophobic side chains. Such associative polymers can form viscous to gelled solutions despite their relatively low molecular weights. Polymers that are soluble can be modified by the addition of a long chain hydrophobic group. A preferred class of such associative polymers is based on nonionic ethylenically unsaturated monomers wherein at least one comonomer has at least 8 carbon atoms.

An example is cetyl hydroxyethylcellulose, available as "NATROSOL PLUS" from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. In hydroalcoholic systems of the present invention, the interpolymer associations can be greatly improved if longer chain hydrophobic groups were used in place of the cetyl groups, since the C16 groups are not as insoluble as longer chain alkyls. For example, alkyl chains containing 18-31 carbon atoms, preferably 20-34 carbon atoms, provide particularly desirable polymeric thickeners in a hydroalcoholic solvent system containing at least a 65:35 alcohol to water ratio. Long chain alkenyl and aralkyl groups may also be suitable.

Polymer/surfactant combinations are also useful thickening agents for compositions of the present invention. These are discussed in detail in U.S. Pat. No. 5,908,619 as well as Novel Gelling Agents Based on Polymer/Surfactant Systems, E. D. Goodard et. al., J. Soc. Cosmet. Chem., 42, 19-34 (January/February, 1991) discloses polymer/surfactant thickener systems for completely aqueous systems based on quaternary polymers in combination with anionic surfactants. The thickening system includes a complex of a charged polymer and an oppositely charged surfactant. This complex is formed as a result of reaction between ionizable groups on both the polymer and the surfactant to form ionic groups on both, which then ionically associate. Preferably, this complex is formed as a result of acid-base reactions of the ionizable groups on the polymer and the surfactant. For example, the polymer can have acidic or basic groups that, when combined with a surfactant having acidic or basic groups neutralizes each other, thereby forming charged species. These charged species then ionically associate to form a complex that comprises the thickening system in the hydroalcoholic compositions of the present invention. The charged surfactant molecules can also hydrophobically associate as a result of the hydrophobic regions of the surfactant. U.S. Pat. No. 5,908,619 specifically refers to systems that utilize a hydroalcoholic vehicle. These same systems may be suitable for aqueous systems without alcohol utilizing ionizable which include hydrophobic side chains that are capable of hydrophobically associating with the ionizable surfactant and/or other hydrophobic side chains of other polymer molecules. Examples of suitable hydrophobic side chains include alkyl side chains having at least 8 carbon atoms, preferably at least 12 carbon atoms, and more preferably at least 16 carbon atoms, polystyrene side chains (typically of 2,000 to 30,000 number average molecular weight), and the like, and mixtures thereof.

Emulsifiers and waxes also may be used to thicken the compositions of the present invention. These systems tend to have an oil phase and a water phase and form a stable emulsion. While preferred compositions of the present invention are iodine stable, inclusion of certain emulsifiers may provide enhanced chemical stability during storage (as evidenced by a reduced loss of available iodine after 6 months @ 40° C.). In the case of biphasic formulations containing the above antimicrobial, the emulsifier and wax thickeners will be preferably employed in an amount within the range of from about 3 weight percent (wt-%) to about 14 wt-%, and more preferably from about 5 wt-% to about 10 wt-%, depending upon the amount of antiseptic and other surfactants employed.

The emulsifier-thickener suitable for use herein may comprise ethers of polyethylene glycol and fatty alcohols, such as non-ionic emulsifying waxes such as POLAWAX and POLAWAX A31 from Croda Co., which contain an alkyl alcohol such as cetyl and stearyl alcohol, in combination with one or more ethoxylated alcohols. A mixture of polyoxyethylene (20) stearyl alcohol ether (BRIJ 78, Uniqema) or Polyoxyethylene (20) cetyl alcohol ether (BRIJ 58, Uniqema) with cetyl or stearyl alcohol. The ratio of the BRIJ or a mixture of the two BRIJ with the fatty alcohol or a mixture of the two alcohols should be within the range of from 0.6 to 3.5, preferably from 1 to 3. Other suitable emulsifier systems include CRODAPHOS CES (Cetearyl Alcohol (and) Dicetyl Phosphate (and) Ceteth-10 Phosphate, Croda USA), Incroquat Behenyl TMS (behentrimonium methosulfate, cetearyl alcohol, Croda USA), non-ionic emulsifiers like polyoxyethylene oleyl ether, PEG-40 stearate, ceteareth-12 (e.g., EUMULGIN B-1 manufactured by Henkel), ceteareth-20 (e.g., EUMULGIN B-2 manufactured by Henkel), ceteareth-30, Lanette O (manufactured by Henkel; ceteareth alcohol), glyceryl stearate (e.g., CUTINA GMS manufactured by Henkel), PEG-100 stearate, ARLACEL 165 (glyceryl stearate and PEG-100 stearate, Uniqema), steareth-2 and steareth-20, or combinations/mixtures thereof, as well as cationic emulsifiers like stearamidopropyl dimethylamine and behentrimonium methosulfate, or combinations/mixtures thereof. Another emulsifier system suitable for use in the lotion or cream of the invention comprises a combination of glyceryl monostearate with polyoxyethylene sorbitan plamitate or stearate and cetyl or stearyl alcohol. For example, an oil in water cream can be made using castor oil (4.5-6%), glyceryl monostearate (4.5-6%), cetyl or stearyl alcohol (9-11%) and TWEEN 60 (polyoxyethylene sorbitan monostearate 2.7-3.5%).

Various combinations of thickening agents and/or film-forming polymers can be used in compositions of the present invention.

Other Optional Ingredients

It may be desirable to include one or more other (secondary) antimicrobial agents as preservatives and/or active ingredients in combination with iodine. Other actives can include cationics such as polyhexamethylene biguanide (PHMB, COSMOCIL CQ from Arch Biocides), chlorhexidine salts such as chlorhexidine gluconate, chlorhexidine acetate, benzethonium chloride, methylbenzethonium chloride, octenidine, cetyl pyridinium chloride, and the like, as well as other cationic antiseptics disclosed in U.S. Patent Application Publication No. 2006/0051384. Natural oil antiseptics such as those disclosed in U.S. Patent Application Publication No. 2006/0051384 may be added. In addition, it may be desirable to add antimicrobial lipids such as those described in U.S. Patent Application Publication No. 2005/0089539, although in certain embodiments, compositions of the present invention do not include antimicrobial lipids. Phenolic type antimicrobials also may be useful such as triclosan, parachlorometaxylenol and others disclosed in U.S. Patent Application Publication No. 2006/0052452.

It also may be desirable to add preservatives such as methyl, ethyl, propyl, and butyl paraben, 2 phenoxyethanol, hydantoins, diazolidinyl urea, and the like.

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, or anti-inflammatory agents), or may contain materials useful in physically formulating various dosage forms of the present invention, such as excipients, dyes, perfumes, lubricants, stabilizers, skin penetration enhancers, preservatives, or antioxidants, flavorants, flavor masking agents, odor masking agents, anti-inflammatories, antioxidants, vitamins, enzymes, enzyme inhibitors, growth factors, and sensates to induce a cool or warm feeling such as menthol, and the like.

Application and Use

The compositions of the present invention are preferably supplied in the ready to use concentration (i.e., can be directly applied to tissue). The compositions may also be prepared as concentrates that are diluted prior to use. For example, concentrates requiring dilution ratios of 0.5:1 to 3:1 parts water to concentrate are contemplated. The higher limit of the concentrate is limited by the solubility and compatibility of the various components at higher concentrations.

The compositions of the present invention may be applied to the skin or to mucosal surfaces (nares, urethra, vagina, etc.) using any suitable means. Ordinarily an absorbent of some type such as gauze, foam sponges, non-woven fabrics, cotton fabrics, cotton swabs or balls, and the like, are soaked with the composition which is used to wipe the composition over the intended site. With very high activity compositions having exceptional wetting properties (e.g., higher alcohol content formulations), a single stroke prep may be all that is necessary. In most cases, however, it is believed that it helps to wipe the soaked absorbent across the skin several times, preferably in various directions, in order to thoroughly wet the skin and ensure good coverage into the finer details of the skin. In general, however, extensive scrubbing is not called for as is recommended by prior art products due to the enhanced activity resulting from the high concentration of organic buffer. For example, the manufacturer of BETADINE Surgical Scrub (Purdue Frederick Company, Norwalk, Conn.) specifies that the user scrub thoroughly for 5 minutes. The compositions of the present invention require scrubbing for less than about 60 seconds, preferably less than about 45 seconds, and most preferably less than about 30 seconds, followed by a 2-minute wait without blotting.

In order to maintain strict asepsis, however, the applier of a preoperative patient skin prep will preferably start at the proposed site of the incision and work outward, thus preventing return to the incision site with a "dirty" applicator. Certain compositions of the present invention can be wiped on the skin in a simple overlapping motion taking care to cover each spot at least two or three times as the user works outward such that essentially no scrubbing is required.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

TABLE 1

| | | Components | | |
|---|---|---|---|---|
| Ingredient | Trade Name | Abbrev. | Manufacturer | City, State |
| Povidone Iodine | Povidone Iodine | PVP-I | BASF | Florham Park, NJ |
| Water | HPLC Grade Water | $H_2O$ | Baxter Healthcare | Deerfield, IL |
| Lactic Acid (90%) | HiPure90 | LA | PURAC | Lincolnshire, IL |
| Sodium iodide | — | NaI | Sigma-Aldrich | St. Louis, MO |
| Lauramido-propylamine/ myristamido-propylamine oxide (30%-33%) | Ammonyx LMDO | AMNX | Stepan | Northfield, IL |
| Malic Acid | — | MA | Universal Preserv-A-Chem, Inc. | Somerset, NJ |
| Sodium hydroxide | — | NaOH | Riedel-de Haen | Seelze, Germany |
| Poly-oxyethylene(100) stearyl ether (CAS: 9005-00-9) | Steareth-100 | hetoxyl STA-100 | Global Seven | Columbus, OH |
| PPG-5-Ceteth-10-Phosphate | Crodafos SG | PPG-5-C-10-P | Croda | Edison, NJ |
| Polyquaternium-10 | Celquat SC-230M | PolyQ-10 | National Starch and Chemical Co, | Bridgewater, NJ |
| Xylitol | Xylisorb | — | Roquette America, Inc. | Keokuk, IA |

Preparation of 10% Povidone Iodine Aqueous Solution

Povidone iodine (100 g, BASF, Florham Park, N.J.) was poured into a 3.8 liter (1 gallon) glass jar containing 900 g water (HPLC grade, Baxter Healthcare, Deerfield, Ill.). A lid was applied and the jar was rolled on a roller over night to allow complete dissolution of the povidone iodine powder. The solution was labeled as "10% PVPI."

Available Iodine Titration Test Method

This method is used to measure the total amount of available iodine ($I_2$) in the formulated samples using the sodium thiosulfate titration of Iodine ($I^0$).

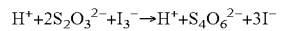
$$H^+ + 2S_2O_3^{2-} + I_3^- \rightarrow H^+ + S_4O_6^{2-} + 3I^-$$

For each sample to be titrated, 3.5 to 4.5 grams (target 4.0 grams) were weighed into a clean 100 mL beaker, and the weight was accurately recorded for calculations. A stir bar was then added to the sample, along with 50 mL of HPLC grade water. The sample was placed on a stir plate to begin stirring. About 1-2 drops of 6N sulfuric acid (ACS grade) were added to each sample to ensure an excess of acid, see chemical expression above.

The samples were continuously stirred until completely dissolved. Samples were then titrated with 0.05 N sodium thiosulfate (standardized immediately before use, RSD<2%) using a Metrohm 799 GPT Titrino automatic titrator with TI 703 stand and a Metrohm platinum electrode (Metrohm 6.0431.100, platinum/pH) available from Metrohm USA of Riverview, Fla.

Acidified water blanks were run in triplicate to ensure the water used contained no iodine. Blanks were prepared by addition of 5 drops of 6N sulfuric acid to 50 mL of HPLC grade water.

The endpoints were automatically determined by the software, and manually verified by visual inspection of the titration curve. The amount of available iodine (wt %) was automatically calculated from the endpoints as follows:

Iodine (meq/g)=[($N_T$×(EP−mL Blank Average))
±Sample Wt. (g)]

Available Iodine (Wt %)=[Iodine (meq/g)×(126.9 g/1000 mL)]×100%

Where:

Each mL of 0.05 N sodium thiosulfate is equivalent to 126.9 g (126.9 g/1000 mL) of iodine $N_T$=normality of sodium thiosulfate titrant EP=sample End Point volume of sodium thiosulfate titration in mL mL Blank=blank End Point volume of sodium thiosulfate titration in mL (if applicable)

Examples 1A-1H

Into each of eight tared 240 mL (8-oz) jars was placed 50 g of 10% PVP-I solution. Each was fitted with a no-leak teflon cap containing approximately 35 g water (Baxter Healthcare, Deerfield, Ill.) and individually labeled as Examples 1A-1H. Then, for Examples 1C, 1D, 1F and 1H, lactic acid (5.0 g as Hipure 90, PURAC, Lincolnshire, Ill.) was added. For Examples 1B, 1D, 1G, and 1H, sodium iodide (2.5 g, Sigma Aldrich, St. Louis, Mo.) was added. Then, Ammonyx LMDO (0.75 g, Stepan, Northfield, Ill.) was added to the contents of Examples 1E, 1F, 1G and 1H. The pH of the resulting solutions was adjusted to 3.2 using 5N NaOH. Finally, additional water was added to the contents of the jars to make the final Example weight equal to 100 g. Table 2 shows the amounts of components in Examples 1A-1H.

Examples 1A-1H were each divided into 4 portions and placed into 0.5 dram borosilicate glass vials available from VWR, West Chester, Pa., and capped with a TEFLON lid. One vial of each Example was analyzed for initial % $I_2$ potentiometrically according to the method described above. The remaining Example 1 vials were placed into a 52° C. oven to simulate aging. One vial of each Example was removed from the oven at the times specified below in Table 3 and analyzed for % $I_2$. The results for the percent remaining $I_2$ in each sample, at each time point, are shown in Table 3. The % $I_2$ values are reported as average values from two titration measurements.

TABLE 3

Examples 1A-1H Percent Remaining $I_2$

| | | Time (hours) | | | |
| --- | --- | --- | --- | --- | --- |
| | | 0 | 119 | 218 | 359 |
| Example | Components | % $I_2$ Remaining | | | |
| 1A | PVP-I | 100 | 98 | 97 | 97 |
| 1B | PVP-I NaI | 100 | 100 | 100 | 100 |
| 1C | PVP-I LA | 100 | 96 | 95 | 93 |
| 1D | PVP-I LA NaI | 100 | 95 | 95 | 93 |
| 1E | PVP-I AMNX | 100 | 98 | 98 | 98 |
| 1F | PVP-I LA AMNX | 100 | 96 | 95 | 93 |
| 1G | PVP-I AMNX NaI | 100 | 100 | 100 | 102 |
| 1H | PVP-I LA AMNX NaI | 100 | 97 | 95 | 97 |

The results of the experiment show that addition of lactic acid (Example 1C) accelerates loss of iodine from povidone iodine solution during the aging study. Addition of 2.5% NaI (Example 1B) or of Ammonyx LMDO (Example 1E) stabilizes povidone iodine solutions. However, NaI and Ammonyx LMDO do not stabilizes povidone iodine solutions significantly in the presence of lactic acid (Examples 1D and 1F). Furthermore, Ammonyx LMDO (Example 1E) stabilizes povidone iodine solution but not in the presence of lactic acid (Example 1F). Finally, the combination of sodium iodide and Ammonyx LMDO (Examples 1G and 1H) significantly improves aging stability of povidone iodine solutions.

Examples 2A-2E

To confirm the results seen in Example 1, the experiment was repeated for the lactic acid containing samples and PVP-I control. New Examples (2A-2E) were prepared and aged at 52° C. over a longer period of time. Examples 2A-2E shown in Table 4 were prepared in a manner identical to those prepared for Examples 1A-1H.

TABLE 2

Examples 1A-1H

| components | 1A* | 1B* | 1C* | 1D* | 1E* | 1F* | 1G* | 1H |
| --- | --- | --- | --- | --- | --- | --- | --- | --- |
| 10% PVPI | 50 g | 50 g | 50 g | 50 g | 50 g | 50 g | 50 g | 50 g |
| LA | — | — | 5 g | 5 g | — | 5 g | — | 5 g |
| NaI | — | 2.5 g | — | 2.5 g | — | — | 2.5 g | 2.5 g |
| AMNX | — | — | — | — | 0.5 g | 0.5 g | 0.5 g | 0.5 g |
| Water | to 100 g | to 100 g | to 100 g | to 100 g | to 100 g | to 100 g | To 100 g | to 100 g |
| pH | 3.2 | 3.2 | 3.2 | 3.2 | 3.2 | 3.2 | 3.2 | 3.2 |

*Comparative Examples

TABLE 4

| components | 2A* | 2B* | 2C* | 2D* | 2E |
|---|---|---|---|---|---|
| 10% PVPI | 50 g | 50 g | 50 g | 50 g | 50 g |
| LA | 0 | 5 g | 5 g | 5 g | 5 g |
| NaI | 0 | 0 | 2.5 g | 0 | 2.5 g |
| AMNX | 0 | 0 | 0 | 0.5 g | 0.5 g |
| Water | to 100 g | to 100 g | to 100 g | To 100 g | to 100 g |
| pH | 3.2 | 3.2 | 3.2 | 3.2 | 3.2 |

*Comparative Examples

Examples 2A-2E were divided into 6 portions, each of which was placed into a vial, capped with a Teflon lid. One vial of each Example 2A-2E was analyzed for initial % $I_2$. The remainder of the samples were placed into a 52° C. oven. One vial of each Example 2 was removed from the oven at the times specified below in table 5 and analyzed for % $I_2$. Results for the percent remaining $I_2$ in each sample, at each time point, are shown in Table 5. The % $I_2$ values are reported as average values from two titration measurements.

TABLE 5

Examples 2A-2E Percent Remaining $I_2$

| Example | Components | \multicolumn{6}{c}{Time (hours)} |
|---|---|---|---|---|---|---|---|

| Example | Components | 0 | 168 | 336 | 504 | 672 | 840 |
|---|---|---|---|---|---|---|---|
| 2A | PVP-I | 100 | 99 | 96 | 95 | 94 | 94 |
| 2B | PVP-I LA | 100 | 95 | 93 | 90 | 90 | 87 |
| 2C | PVP-I LA NaI | 100 | 95 | 91 | 91 | 90 | 92 |
| 2D | PVP-I LA LMDO | 100 | 94 | 90 | 88 | 89 | 87 |
| 2E | PVP-I LA LMDO NaI | 100 | 96 | 95 | 94 | 94 | 94 |

The results for Examples 2A-2E confirmed the results for Examples 1A-1H. The addition of lactic acid (Example 2B) accelerated the loss of $I_2$ from the samples compared to the PVP-I alone (Example 2A). Addition of sodium iodide (Example 2C) improved the stability of $I_2$ in the presence of lactic acid. However, the addition of both Ammonyx LMDO and NaI (Example 2E) provided the best stability in the presence of lactic acid over 5 weeks at 52° C.

Examples 3A-3E

Examples 3A-3E, shown in Table 6 below, compare the stability of samples containing PVP-I, lactic acid and malic acid stabilized with Ammonyx LMDO to identical samples stabilized with both NaI and Ammonyx LMDO.

Examples 3A-3E were prepared by adding water into a glass container and stirring slowly using an electric-powered overhead propeller stirrer. Next, lactic acid, malic acid, sodium hydroxide pellets, hetoxyl STA-100, and Crodafos SG were added sequentially with stirring until dissolved and before adding the subsequent reagent. The speed of stirring was then dramatically increased prior to slow addition of Celquat SC-230M into the vortex. The solutions were stirred rapidly for 1 hour. Then, xylitol was added with rapid stirring until dissolved, followed by addition of Ammonyx LMDO, povidone iodine, and sodium iodide. The pH of the resulting solutions were measured and then adjusted to pH=3.2 with 6N NaOH, taking care to stir in the base very well to prevent iodine degradation. Finally, water was added to bring the formulations to the target weight.

TABLE 6

Examples 3A-3E

| Component | 3A | 3B | 3C | 3D* | 3E* |
|---|---|---|---|---|---|
| 10% PVP-I | 5 | 5 | 5 | 5 | 5 |
| PPG-5-C-10-P | 1 | 1 | 1 | 1 | 1 |
| AMNX | 0.75 | 0.75 | 0.75 | 0.75 | 0.75 |
| Steareth-100 | 1.4 | 1.4 | 0 | 0 | 1.4 |
| LA | 5 | 7 | 5 | 5 | 5 |
| MA | 2 | 0 | 2 | 2 | 2 |
| Xylitol | 10 | 10 | 10 | 10 | 10 |
| PolyQ-10 | 1 | 1 | 1 | 1 | 1 |
| NaOH | 0.8 | 0.8 | 0.8 | 0.8 | 0.8 |
| NaI | 2.5 | 2.5 | 2.5 | 0 | 0 |
| Purified water | 70.55 | 70.55 | 71.95 | 74.45 | 73.05 |
| Total | 100 | 100 | 100 | 100 | 100 |
| pH | 3.2 | 3.2 | 3.2 | 3.2 | 3.2 |

*Comparative Examples

For Examples 3A, 3B, 3C, and 3D, each of the samples was divided into 7 gram portions and placed into glass or HDPE containers; more specifically into 0.5 dram borosilicate glass vials available from VWR, West Chester, Pa., and capped with a Teflon lid; or into 7.4 mL (¼ oz) round HDPE bottles, available from SKS-Bottle, Watervliet, N.Y., and capped with polyethylene-lined, polypropylene caps. The Examples 3A-3D were analyzed for initial % $I_2$ potentiometrically. The remainder of the Examples 3A-3D was placed into ovens at 40° C., 50° C., 60° C., and 70° C. Two of each Example in each container were removed from the ovens at 0, 3.6, 9.7, 13.7, 21, and 27 days and analyzed for % $I_2$. The percent remaining $I_2$, as compared to the initial result (time=0) for samples 3A, 3B, 3C and 3D is reported in Tables 7-10 for each temperature. The values are the average of two measurements.

TABLE 7

Examples 3A-3D in HDPE and Glass at 40° C.

| Example | \multicolumn{6}{c}{Time (days) at 40° C.} |
|---|---|---|---|---|---|---|

| Example | 0 | 3.6 | 9.7 | 13.7 | 21 | 27 |
|---|---|---|---|---|---|---|
| 3A in HDPE | 100 | 99 | 97 | 96 | 96 | — |
| 3B in HDPE | 100 | 97 | 97 | 96 | 95 | 95 |
| 3C in HDPE | 100 | 100 | 98 | 98 | 97 | 93 |
| 3D in HDPE | 100 | 99 | 97 | 97 | 95 | 94 |
| 3A in glass | 100 | 99 | 97 | 97 | 96 | 95 |
| 3B in glass | 100 | 99 | 98 | 97 | 97 | 96 |
| 3C in glass | 100 | 100 | 99 | 99 | 98 | 97 |
| 3D in glass | 100 | 100 | 99 | 98 | 97 | 95 |

TABLE 8

Examples 3A-3D in HDPE and Glass at 50° C.

| Example | Time (days) at 50° C. | | | | |
|---|---|---|---|---|---|
| | 0 | 3.6 | 9.7 | 13.7 | 21 | 27 |
| 3A in HDPE | 100 | 97 | 95 | 94 | 94 | — |
| 3B in HDPE | 100 | 96 | 95 | 94 | 94 | 94 |
| 3C in HDPE | 100 | 96 | 94 | 87 | 90 | 86 |
| 3D in HDPE | 100 | 97 | 90 | 88 | 84 | 78 |
| 3A in glass | 100 | 97 | 95 | 95 | 94 | 94 |
| 3B in glass | 100 | 96 | 95 | 95 | 95 | 94 |
| 3C in glass | 100 | 95 | 96 | 87 | 89 | 85 |
| 3D in glass | 100 | 98 | 94 | 91 | 87 | 82 |

TABLE 9

Examples 3A-3D in HDPE and Glass at 60° C.

| Example | Time (days) at 60° C. | | | | |
|---|---|---|---|---|---|
| | 0 | 1 | 3 | 5.8 | 8.1 | 13.7 |
| 3A in HDPE | 100 | 96 | 97 | 96 | 96 | 95 |
| 3B in HDPE | 100 | 96 | 98 | 97 | 100 | 104 |
| 3C in HDPE | 100 | 98 | 99 | 91 | 88 | 82 |
| 3D in HDPE | 100 | 97 | 94 | 88 | 84 | 68 |
| 3A in glass | 100 | 97 | 95 | 95 | 95 | 93 |
| 3B in glass | 100 | 96 | 95 | 94 | 94 | 94 |
| 3C in glass | 100 | 98 | 96 | 88 | 85 | 81 |
| 3D in glass | 100 | 97 | 93 | 88 | 85 | 71 |

TABLE 10

Examples 3A-3D in HDPE and Glass at 70° C.

| Example | Time (days) at 70° C. | | | | |
|---|---|---|---|---|---|
| | 0 | 1 | 3 | 5.8 | 8.1 | 13.7 |
| 3A in HDPE | 100 | 94 | 92 | 89 | 87 | 79 |
| 3B in HDPE | 100 | 94 | 93 | 92 | 91 | 87 |
| 3C in HDPE | 100 | 95 | 84 | 76 | 75 | 66 |
| 3D in HDPE | 100 | 90 | 78 | 57 | 51 | 34 |
| 3A in glass | 100 | 95 | 93 | 94 | 92 | 83 |
| 3B in glass | 100 | 95 | 93 | 93 | 92 | 88 |
| 3C in glass | 100 | 96 | 84 | 79 | 81 | 68 |
| 3D in glass | 100 | 93 | 82 | 67 | 58 | 39 |

Example 3E

Example 3E was compounded on a different date in the same manner described for Examples 3A-3D, and aging was conducted in a separate study. An amount of 10 g portions of Example 3E were packaged into glass vials (borosilicate glass vials, VWR, West Chester, Pa.), and capped with a Teflon lid. Initial samples of were analyzed for initial % $I_2$ (potentiometrically). The remainder of the samples was placed into ovens at 40° C., 60° C., and 70° C. The results for percent remaining $I_2$ at each time point are reported in Table 11.

TABLE 11

Example 3E % $I_2$ remaining storage in glass at 40° C., 60° C., and 70° C.

| Temperature | Time (days) | | | | |
|---|---|---|---|---|---|
| | 0 | 2.7 | 5.1 | 18 | 29.8 |
| 40° C. | 100 | 100 | 99 | 95 | 93 |
| 60° C. | 100 | 95 | 91 | 78 | 70 |
| 70° C. | 100 | 83 | 73 | 43 | 28 |

Figure 2:
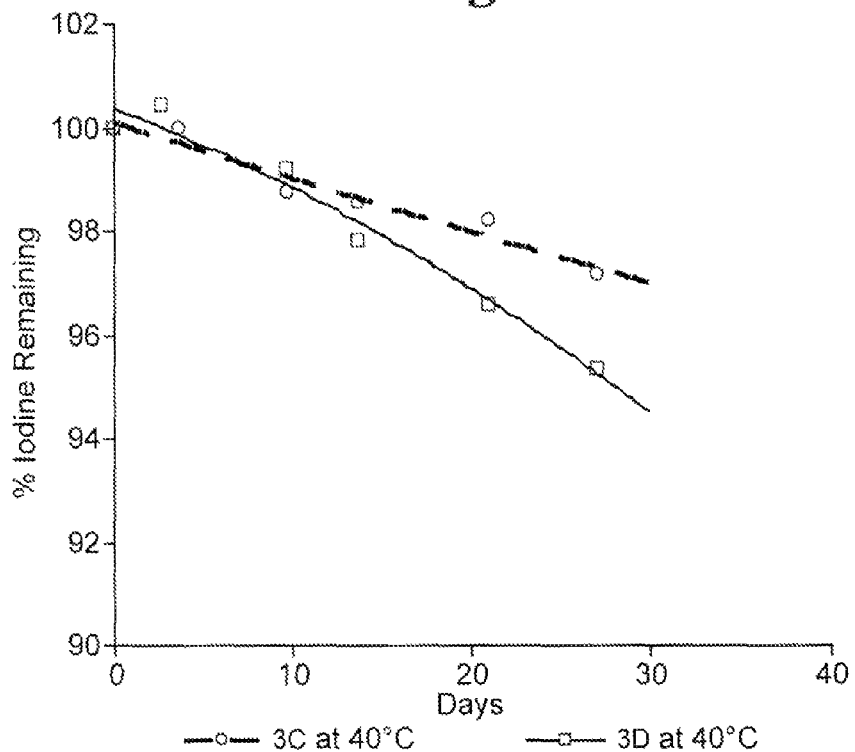
FIG. 2 is a graphical representation of the loss of available iodine over time according to Examples 3C and 3D.

Examples 3A and 3E are identical except that Example 3A contains NaI. Similarly, Examples 3C and 3D are identical, except that Example 3C contains NaI. See FIG. 1 for a comparison of stability of Example 3A vs. 3E. See FIG. 2 for a comparison of Example 3C vs. 3D.

Examples 4A-4C

Examples 4A-4C were identical compositions and were prepared in the same manner as Example 3A. Chemical and physical stability was measured over time and are reported below.

TABLE 12

Examples 4A-4C % $I_2$ Remaining - Stability Data

| Examples | 0 | 1 | 2 | 3 | 6 | 9 |
|---|---|---|---|---|---|---|
| Months at 25° C./60% RH | | | | | | |
| 4A | 100 | — | — | 98 | 98 | 98 |
| 4B | 100 | — | — | 100 | 100 | 100 |
| 4C | 100 | — | — | 98 | 98 | 100 |
| Months at 30° C./75% RH | | | | | | |
| 4A | 100 | — | — | 98 | 98 | 100 |
| 4B | 100 | — | — | 98 | 98 | 100 |
| 4C | 100 | — | — | 98 | 98 | 98 |
| Months at 40° C./75% RH | | | | | | |
| 4A | 100 | 96 | 96 | 96 | 98 | — |
| 4B | 100 | 96 | 98 | 96 | 98 | — |
| 4C | 100 | 96 | 96 | 96 | 98 | — |

Viscosity Test Method

After storage for 0 to 9 months at the conditions shown in Table 13, the viscosities of Examples 4A-4C were measured using a Brookfield viscometer, model LVT with Brookfield LV spindles. All Examples were allowed to equilibrate at approximately 22° C. for 24 hours prior to measurement. Preferably the smallest spindle and the lowest speed were chosen such that the viscosity was taken at the lowest speed possible while staying within 10-90% and preferably 20-80% of the viscometer range. In all cases the sample size and container geometry were chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The viscosity of each sample was taken as the highest relatively stable reading that was achieved.

TABLE 13

Example 4 Viscosity Data in Centipoise, cps

| Examples | 0 | 1 | 2 | 3 | 6 | 9 |
|---|---|---|---|---|---|---|
| Months at 25° C./60% RH | | | | | | |
| 4A | 5675 | — | — | 5650 | 5315 | 4990 |
| 4B | 5275 | — | — | 4695 | 4730 | 4775 |
| 4C | 5150 | — | — | 4605 | 4620 | 4395 |
| Months at 30° C./75% RH | | | | | | |
| 4A | 5675 | — | — | 4225 | 3980 | 3555 |
| 4B | 5275 | — | — | 4245 | 3820 | 3440 |
| 4C | 5150 | — | — | 4045 | 3665 | 3255 |
| Months at 40° C./75% RH | | | | | | |
| 4A | 5675 | 4140 | 3090 | 2165 | 1013 | — |
| 4B | 5275 | 4160 | 2720 | 1787.5 | 960 | — |
| 4C | 5150 | 4145 | 2585 | 1767 | 918 | — |

Minimum Bactericidal Concentration (MBC) Test Method

This method determines the Minimum Bactericidal Concentration (MBC) for the iodophor-containing tissue antiseptic composition and a commercially available iodophor-containing product (Betadine). The minimum concentration of each product that resulted in the complete kill of an organism following a 30 minute contact time was reported as the MBC. Each dilution series for each organism was performed in triplicate, and a range of concentrations is reported to reflect the minimum and maximum value for MBC obtained among the triplicate experiments.

Test Organisms:

MBC values were determined for 29 bacterial and yeast strains. Microorganisms were selected to include one American Type Culture Collection (ATCC) strain and one clinical isolate strain of each microorganism species tested. Several antibiotic resistant organisms were also tested. The 29 organisms are listed along with the resulting MBC values in table 14.

Preparation of Test Materials for MBC Determination:

For the test iodophor-containing tissue antiseptic composition (5% PVP-I), 2.0 mL of the composition was diluted with 18.0 mL of injection-grade water and mixed well. 14.0 mL of the resulting dilution was further diluted with 46.0 mL of injection grade water and mixed well. The resulting solution contained 128 μg/mL of available iodine.

For the commercial composition, Betadine (10% PVP-I), 2.0 mL of Betadine was diluted with 18.0 mL of injection-grade water and mixed well. An amount of 6.1 mL of the resulting dilution was further diluted in 43.9 mL of injection grade water and mixed well. The resulting solution contained 128 μg/mL of available iodine.

Due to the volatile nature of iodine, product dilutions were prepared <60 minutes prior to their transfer into the test plates, and all solutions were kept tightly capped.

Preparation of Receiver Plates:

Aliquats of 200 μL of appropriate recovery media (determined as described above) was added to each well in rows A, B, G, and H of a 96 well microtiter plate. Two receiver plates were prepared for each challenge microorganism for each sample.

Verification of Neutralization in Receiver Plates:

Neutralization of the tissue antiseptic compositions was accomplished by diluting aliquots of each product from the antiseptic plates into nutrient broth in the neutralizer comprising (if appropriate) receiver plates. Verification of neutralization was performed vs. 23 microorganism strains (at least one isolate within each species). Verification was conducted by transferring ~5 μL of product from an antiseptic plate into a receiver plate inoculated with ~$10^2$ CFU/mL of each tested microorganism. Growth in all wells following incubation of the receiver plate was evidence of adequate neutralization. An appropriate neutralizer for each microorganism was selected based on these results Preparation of Antiseptic Plates:

Two antiseptic 96 well microtiter plates were prepared for each microorganism for each sample. For each antiseptic plate, 100 μL of injection-grade water was added to each well in Columns 2-11, rows A, B, G, and H. A 200 μL aliquot of product, prepared as described previously (128 μg/mL available iodine concentration), or injection-grade water was added to each of the appropriate wells in Column 1. Using a multi-channel pipetter, 100 μL was transferred from each well in Column 1 to the corresponding well in Column 2 (Rows A, B, G, and H), and the solution was mixed in Column 2 by aspirating three times. Pipet tips were changed, and 100 μL aliquots were then transferred from Column 2 into the wells of Column 3. These steps were repeated for Columns 4-11, using new pipet tips for each transfer. After completing the series of dilution across columns 4-11, 100 μL was removed from Column 11, and was discarded so that each well contains a total volume of 100 uL. 200 μL of injection-grade water was added to the wells in Column 12 (Rows A, B, G, and H) to serve as sterility controls.

Preparation of Microorganisms:

For all organisms except *Haemophilus influenzae* ATCC #33391, *Streptococcus pneumoniae* clinical isolate, *Streptococcus pyrogenes*, and *Bacteroides fragilis* ATCC #25285:

Approximately 48 hours prior to testing, separate sterilized tubes containing the appropriate broth media were inoculated from lyophilized vials or cryogenic stock cultures containing each microorganism. Cultures were incubated at the appropriate temperature for each species for 24 hours or until sufficient growth was observed. Approximately 24 hours before testing, the broth cultures were inoculated onto the surface of appropriate solid media in Petri dishes and incubated appropriately until sufficient growth was observed, producing lawns of bacteria or yeast on the surface of the agar plates. Growth from these plates was used to prepare challenge suspensions. Purity of each broth culture was verified by preparing isolation streaks of each culture on appropriate agar medium, and incubating under appropriate conditions for each organism.

For *Haemophilus influenzae* ATCC #33391, *Streptococcus pneumoniae* clinical isolate and *Streptococcus pyrogenes* clinical isolate:

Approximately 48 hours prior to testing, inocula from lyophilized vials or cryogenic stock cultures containing each microorganism were suspended in phosphate buffered saline (PBS), inoculated onto the surface of appropriate agar media in Petri dishes, and incubated at 35±2° C. under appropriate conditions for approximately 24 hours or until sufficient growth was observed. Approximately 24 hours before testing, a suspension of each species was prepared by rinsing the cultures from the solid media with sterile PBS. Purity of species was verified by preparing isolation streaks of each culture on appropriate agar medium and incubating under appropriate conditions for each organism. Aliquots of each suspension were spread-plated onto the surface of additional plates of the appropriate solid medium and incubated appropriately until sufficient growth was observed. The lawns of bacteria produced were used to prepare the challenge suspensions.

For *Bacteroides fragilis* ATCC #25285:

Approximately 48 hours prior to testing, separate sterilized tubes containing Schaedler's Broth (SB) media were inoculated from lyophilized vials or cryogenic stock cultures containing each microorganism. Cultures were incubated anaerobically at 35±2° C. for 24 hours, or until sufficient growth was observed. Approximately 24 hours before testing, the broth cultures were subcultured into additional tubes containing SB and incubated anaerobically at 35±2° C. for 24 hours or until sufficient growth was observed. The purity of each broth culture was verified by preparing isolation streaks on Chocolate Agar with Enrichment (CAE) and incubating aerobically as well as anaerobically. Following incubation, challenge suspensions of this species were prepared by centrifuging both the broth cultures, combining the resulting pellets, and resuspending them in SB.

Inoculation of Antiseptic Plates:

Using a multi-channel pipetter, each well in columns 1-11 (Rows A, B, G, and H) was inoculated with 100 µL of challenge suspension, prepared as described above, to yield approximately $5 \times 10^5$ CFU/mL. Wells in column 12 were not inoculated. Timing was started upon inoculation of Column 11. Plates were covered with sterile lids and incubated at 35 C±2° C. for 30±1 minutes Transfer of Samples to Receiver Plates:

A 96-well pin replicator was flame sterilized and cooled prior to use. Using the sterile replicator, approximately 5 µL of sample were transferred from each inoculated antiseptic plate to the corresponding wells of the receiver plate. The replicator was sterilized between each use.

Incubation of Receiver Plates:

Receiver plates were incubated at appropriate temperatures and conditions for each challenge organism until growth in the control wells (Rows G and H) was visible. The presence of growth was determined visually based on turbidity.

Verification of Test Organism Concentration:

The concentration of each challenge microorganism was verified by plate count immediately following inoculation of the antiseptic plates and prior to incubation. A 10 µL aliquot was removed from two wells in each row, G or H, of each antiseptic plate inoculated with each microorganism. Each sample was transferred to a separate tube containing 10 mL of phosphate buffered water (PBW) and mixed. 100 µL of this dilution was plated using appropriate growth medium. Plates were incubated at appropriate temperatures and conditions for each challenge organism until sufficient growth was observed. An average count of 30 to 200 CFU was considered acceptable.

Method of assessment of MBC:

Following incubation, the receiver plates were examined for growth, visually, on the basis of turbidity. Growth was recorded as a (+). No growth was recorded as a (−). The MBC for each product was reported as the lowest concentration of available iodine that produced complete kill of the microorganism following a 30 minute contact time. For the test to be considered valid, the growth controls must demonstrate growth, the sterility controls must demonstrate no growth, and the challenge microorganism must be at a concentration within the range of 30 to 300 CFU/plate.

MBC Results:

The tissue antiseptic material tested was the same composition as Example 3A. The Betadine was manufactured by Purdue Products (Stamford, Conn.) and contained 10% PVP-I (1% Available iodine) as its active ingredient, along with the following inactive ingredients: pareth 25-9, purified water and sodium hydroxide. Results of the MBC for the test antiseptic Example 3A and Betadine are shown in Table 14.

TABLE 14

MBC Results for Example 3A vs. Betadine

| Microorganism | Strain Identification (ATCC or ID#) | Ex. 3A MBC (µg/mL of Available iodine) | Betadine MBC (µg/mL of available iodine) |
|---|---|---|---|
| *Acinetobacter baumannii* | 032107Ab7 | 0.25-1 | 0.5-2 |
| *Bacteroides fragilis* | 25285 | 0.25 | 0.5-1 |
| *Burkholderia cepacia* | 35254 | 0.5 | 0.5-1 |
| *Haemophilus influenzae* | 33391 | ≤0.063-0.125 | ≤0.063-0.125 |
| *Enterobacter cloacae* | 13047 | 0.25 | 0.25-0.5 |
| *Escherichia coli* | 11229 | 0.5 | 0.5-1 |
| *Klebsiella pneumoniae.* | 111705Kpn8 | 0.25 | 0.25-0.5 |
| *Pseudomonas aeruginosa* | 15442 | 0.5-1 | 0.5-1 |
| *Proteus mirabilis* | 112905Pm23 | 0.5 | 0.5-1 |
| *Serratia marcescens* | 112905Sm26 | 0.5 | 0.5 |
| *Staphylococcus aureus* | 120607MRSa47 | 0.125 | 0.125-0.25 |
| *Staphylococcus aureus* | 29213 | 0.25-1 | 0.5-2 |
| *Staphylococcus aureus* (MRSA) | 33592* | 0.125-0.25 | 0.25 |
| *Staphylococcus aureus* (MRSA) | 43300* | 0.5 | 1 |
| *Staphylococcus aureus* (CA-MRSA or HA-MRSA) | BAA-1556* USA300 | 0.25 | 0.25-0.5 |
| *Staphylococcus aureus* (MRSA) | BAA-811* | 0.25-0.5 | 0.5 |
| *Staphylococcus epidermidis* | 12228 | 0.25 | 0.5 |
| *Staphylococcus epidermidis* (MRSE) | 51625* | 0.125 | 0.125 |
| *Micrococcus luteus* | 071906Ms11 | 0.25 | 0.25-0.5 |
| *Streptococcus pyogenes* | 071906Spy4 | 0.5-1 | 1-2 |
| *Enterococcus faecalis* | 29212 | 0.5-1 | 1 |
| *Enterococcus faecalis* (VRE) | 51299* | 0.5-1 | 1-2 |
| *Enterococcus faecium* | 19434 | 0.5-1 | 2 |
| *Enterococcus faecium* (MDR; VRE) | 51559* | 0.25 | 0.5 |
| *Streptococcus pneumoniae* | 011706Spn17 | 0.5 | 1 |
| *Candida albicans* | 18804 | 2 | 4 |
| *Candida albicans* | 011706Ca26 | 2 | 4 |
| *Candida tropicalis* | 42678 | 2 | 2 |
| *Candida tropicalis* | 011706Ct2 | 2 | 4 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A tissue antiseptic composition comprising:
an antimicrobial agent which is an iodophor, wherein the iodophor is povidone-iodine, wherein the antimicrobial agent is present in a sufficient concentration to provide an available iodine concentration of 0.1 wt-% to 2 wt-%;
a hydroxycarboxylic acid present at a concentration of at least 2.5 wt-%;
an amine oxide; and
an iodide salt present in at least a concentration of 2.0 wt-% and at an amount of no greater than 10 wt-%,
wherein the composition is ready to use, and
wherein the composition exhibits a decrease in available iodine of no greater than 5% wt/wt when stored at 40° C. for about 6 months.

2. The tissue antiseptic composition of claim 1, wherein the hydroxycarboxylic acid is present in an amount greater than 5 wt-%.

3. The tissue antiseptic composition of claim 1, wherein the amine oxide is present in a concentration of 0.25 wt-% to 1.5 wt-%.

4. The tissue antiseptic composition of claim 1, further comprising a monosaccharide, a sugar alcohol, or a combination thereof, wherein the monosaccharide, sugar alcohol, or combination thereof is present at a concentration of greater than 5% wt/wt.

5. The tissue antiseptic composition of claim 4, wherein the composition comprises xylitol.

6. The tissue antiseptic composition of claim 1, further comprising a surfactant; wherein the surfactant comprises an anionic surfactant, an amphoteric surfactant, a nonionic surfactant, a zwitterionic surfactant, or a combination thereof; wherein the anionic surfactant comprises a phosphate, phosphonate, sulfate, sulfonate, or a combination thereof.

7. The tissue antiseptic composition of claim 1 further comprising a vehicle, wherein the vehicle comprises water.

8. The tissue antiseptic composition of claim 7 wherein the vehicle further comprises a polyethylene glycol having a molecular weight of less than 1500.

9. The tissue antiseptic composition of claim 1 further comprising a thickener.

10. A tissue antiseptic composition comprising:
an antimicrobial agent which is an iodophor, wherein the iodophor is povidone-iodine, wherein the antimicrobial agent is present in a sufficient concentration to provide an available iodine concentration of 0.1 wt-% to 2 wt-%;
a monosaccharide, a sugar alcohol, or a combination thereof;
a surfactant;
water;
a thickener;
a hydroxycarboxylic acid present at a concentration of greater than 1.0 wt-%; an amine oxide; and
an iodide salt present at a concentration of greater than 2.0 wt-% to 10 wt-%,
wherein the composition is ready to use and wherein the composition is iodine stable, and
wherein the composition exhibits a decrease in available iodine of no greater than 5% wt/wt when stored at 40° C. for about 6 months.

11. The tissue antiseptic of claim 10, wherein the surfactant is an anionic surfactant, a zwitterionic surfactant, or a combination thereof, wherein the anionic surfactant is a phosphate, phosphonate, sulfate, sulfonate, or a combination thereof.

12. The tissue antiseptic composition of claim 10 further comprising a polyethylene glycol having a molecular weight of less than 1500.

13. The tissue antiseptic composition of claim 10, wherein the amine oxide is present at a concentration of 0.25 wt-% to 1.5 wt-%.

14. The tissue antiseptic composition of claim 10 comprising xylitol.

15. The tissue antiseptic composition of claim 10, wherein the monosaccharide, sugar alcohol, or combination thereof is present at a concentration of greater than 5% wt/wt.

16. A method of decolonizing the nasal passages of a subject, the method comprising applying the composition of claim 1 to the nasal passages of the subject.

17. A method of disinfecting the tissue of a subject, the method comprising applying the composition of claim 1 to the tissue of the subject.

18. A method of stabilizing a tissue antiseptic composition comprising an iodophor and a hydroxycarboxylic acid, the method comprising:
providing a tissue antiseptic composition comprising; an antimicrobial agent which is an iodophor, wherein the iodophor is povidone-iodine, wherein the antimicrobial agent is present in a sufficient concentration to provide an available iodine concentration of 0.1 wt-% to 2 wt-%; and a hydroxycarboxylic acid present at concentration of greater than 2.5 wt-%;
providing an amine oxide and an iodide salt;
mixing the amine oxide and the iodide salt with the tissue antiseptic composition to form a stabilized composition, wherein the amine oxide is present in the stabilized composition at a total concentration of 0.25 wt-% to 1.5 wt-% and the iodide salt is present in the stabilized composition at a total concentration of about 1.5 wt-% to 10 wt-%,
wherein the composition exhibits a decrease in available iodine of no greater than 5% wt/wt when stored at 40° C. for about 6 months.

* * * * *

UNITED STATES PATENT AND TRADEMARK OFFICE
CERTIFICATE OF CORRECTION

PATENT NO. : 8,808,722 B2  
APPLICATION NO. : 13/807035  
DATED : August 19, 2014  
INVENTOR(S) : Matthew Scholz Page 1 of 2

It is certified that error appears in the above-identified patent and that said Letters Patent is hereby corrected as shown below:

In the Specification

Column 1  
Line 56, Delete "hydoxycarboxylic" and insert -- hydroxycarboxylic --, therefor.

Column 2  
Line 11-12, Delete "monosaccarides" and insert -- monosaccharides --, therefor.

Column 4  
Line 31, Delete "loose" and insert -- lose --, therefor.

Column 6  
Line 1, Delete "musocal" and insert -- mucosal --, therefor.  
Line 63, Delete "and or" and insert -- and/or --, therefor.

Column 10  
Line 13, Delete "sufactant(s)" and insert -- surfactant(s) --, therefor.  
Line 55, Delete "polyalklylene" and insert -- polyalkylene --, therefor.

Column 11  
Line 1, Delete "N,N' diakyl" and insert -- N,N'-dialkyl --, therefor.  
Line 38, Delete "povidone--iodine" and insert -- povidone-iodine --, therefor.  
Line 50, Delete "monosaccarides" and insert -- monosaccharides --, therefor.  
Line 55, Delete "ribose" and insert -- ribose. --, therefor.

Column 12  
Line 46, Delete "and or" and insert -- and/or --, therefor.

Signed and Sealed this  
Thirtieth Day of December, 2014

Michelle K. Lee  
*Deputy Director of the United States Patent and Trademark Office*

CERTIFICATE OF CORRECTION (continued)

U.S. Pat. No. 8,808,722 B2

Column 13
Line 26, Delete "Barret" and insert -- Barrett --, therefor.
Line 57, Delete "Polaxamers." and insert -- Poloxamers. --, therefor.

Column 15
Line 13, Delete "lease" and insert -- least --, therefor.
Line 39, Delete "sufonates," and insert -- sulfonates, --, therefor.

Column 16
Line 17, Delete "Phosponates." and insert -- Phosphonates. --, therefor.
Line 36-37, Delete "Parsipanny," and insert -- Parsippany, --, therefor.

Column 21
Line 21-22, Delete "carragheenin," and insert -- carrageenan, --, therefor.
Line 33, Delete "polyquaterium" and insert -- polyquaternium --, therefor.

Column 22
Line 59, Delete "dimethyldiallyammonium" and insert -- dimethyldiallylammonium --, therefor.

Column 24
Line 56, Delete "plamitate" and insert -- palmitate --, therefor.

Column 27
Line 23, Delete "±Sample" and insert -- ÷ Sample --, therefor

Column 33
Line 56, Delete "Aliquats" and insert -- Aliquots --, therefor.

Column 34
Line 6, Delete "results" and insert -- results. --, therefor.
Line 16, Delete "pipetter," and insert -- pipette, --, therefor.

Column 35
Line 14-15, Delete "centrifµging" and insert -- centrifuging --, therefor.
Line 18, Delete "pipetter," and insert -- pipette, --, therefor.
Line 24, Delete "minutes" and insert -- minutes. --, therefor.

In the Claims

Column 38
Line 6, Claim 11, delete "antiseptic of" and insert -- antiseptic composition of --, therefor.